(12) United States Patent
Hirakawa

(10) Patent No.: US 8,403,829 B2
(45) Date of Patent: Mar. 26, 2013

(54) ENDOSCOPIC FORM DETECTION DEVICE AND FORM DETECTING METHOD OF INSERTION SECTION OF ENDOSCOPE

(75) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 19 days.

(21) Appl. No.: 13/242,415

(22) Filed: Sep. 23, 2011

(65) Prior Publication Data

US 2012/0053412 A1 Mar. 1, 2012

Related U.S. Application Data

(63) Continuation of application No. PCT/JP2011/063736, filed on Jun. 15, 2011.

(30) Foreign Application Priority Data

Aug. 27, 2010 (JP) ................................ 2010-191350

(51) Int. Cl.
*A61B 1/005* (2006.01)

(52) U.S. Cl. ........................................ 600/117; 600/145

(58) Field of Classification Search .................. 600/117, 600/118, 145, 424
See application file for complete search history.

(56) References Cited

U.S. PATENT DOCUMENTS

| 6,059,718 | A | 5/2000 | Taniguchi et al. | |
|---|---|---|---|---|
| 6,612,992 | B1 * | 9/2003 | Hossack et al. | 600/467 |
| 6,773,394 | B2 * | 8/2004 | Taniguchi et al. | 600/117 |
| 7,277,833 | B2 * | 10/2007 | Kukuk | 703/2 |
| 7,865,229 | B2 * | 1/2011 | Horn | 600/424 |
| 8,147,402 | B2 * | 4/2012 | Tanaka et al. | 600/117 |
| 8,211,010 | B2 * | 7/2012 | Hirakawa | 600/118 |
| 8,298,136 | B2 * | 10/2012 | Kimura et al. | 600/117 |
| 2004/0116775 | A1 * | 6/2004 | Taniguchi et al. | 600/117 |
| 2007/0106114 | A1 * | 5/2007 | Sugimoto et al. | 600/117 |
| 2007/0106116 | A1 * | 5/2007 | Sugimoto | 600/117 |
| 2010/0191056 | A1 * | 7/2010 | Tanaka | 600/117 |
| 2011/0098533 | A1 * | 4/2011 | Onoda et al. | 600/117 |
| 2011/0313414 | A1 | 12/2011 | Liu et al. | |
| 2012/0059221 | A1 | 3/2012 | Hirakawa | |

FOREIGN PATENT DOCUMENTS

| JP | A-11-019027 | 1/1999 |
|---|---|---|
| JP | A-2000-175862 | 6/2000 |

(Continued)

OTHER PUBLICATIONS

Jun. 25, 2012 Supplementary Search Report issued in European Patent Application No. 11813645.6.
International Search Report issued in International Application No. PCT/JP2011/063736 dated Jul. 19, 2011 (with translation).

*Primary Examiner* — John P Leubecker
(74) *Attorney, Agent, or Firm* — Oliff & Berridge PLC

(57) ABSTRACT

An endoscopic form detection device includes a sensor tentative position detecting section configured to detect a tentative position of each sensor unit on the assumption that a portion between the respective sensor units is a linear tentative link whose dimension is equal to an inter-sensor dimension. The endoscopic form detection device includes a sensor position correcting section configured to correct a position of each sensor unit from the tentative position to a final position based on an absolute value of a difference between an arc length of each tentative arc and the inter-sensor dimension, and a final curve form detecting section configured to perform curve interpolation between the final positions of the respective sensor units by using a final arc to detect a final curve form of an inserting section.

14 Claims, 15 Drawing Sheets

FOREIGN PATENT DOCUMENTS

| | | |
|---|---|---|
| JP | A-2007-130154 | 5/2007 |
| JP | A-2007-130175 | 5/2007 |
| WO | WO 2009/097461 A1 | 8/2009 |
| WO | WO 2009/146654 A1 | 12/2009 |
| WO | WO 2011/152140 A1 | 12/2011 |
| WO | WO 2012/026184 A1 | 3/2012 |

* cited by examiner

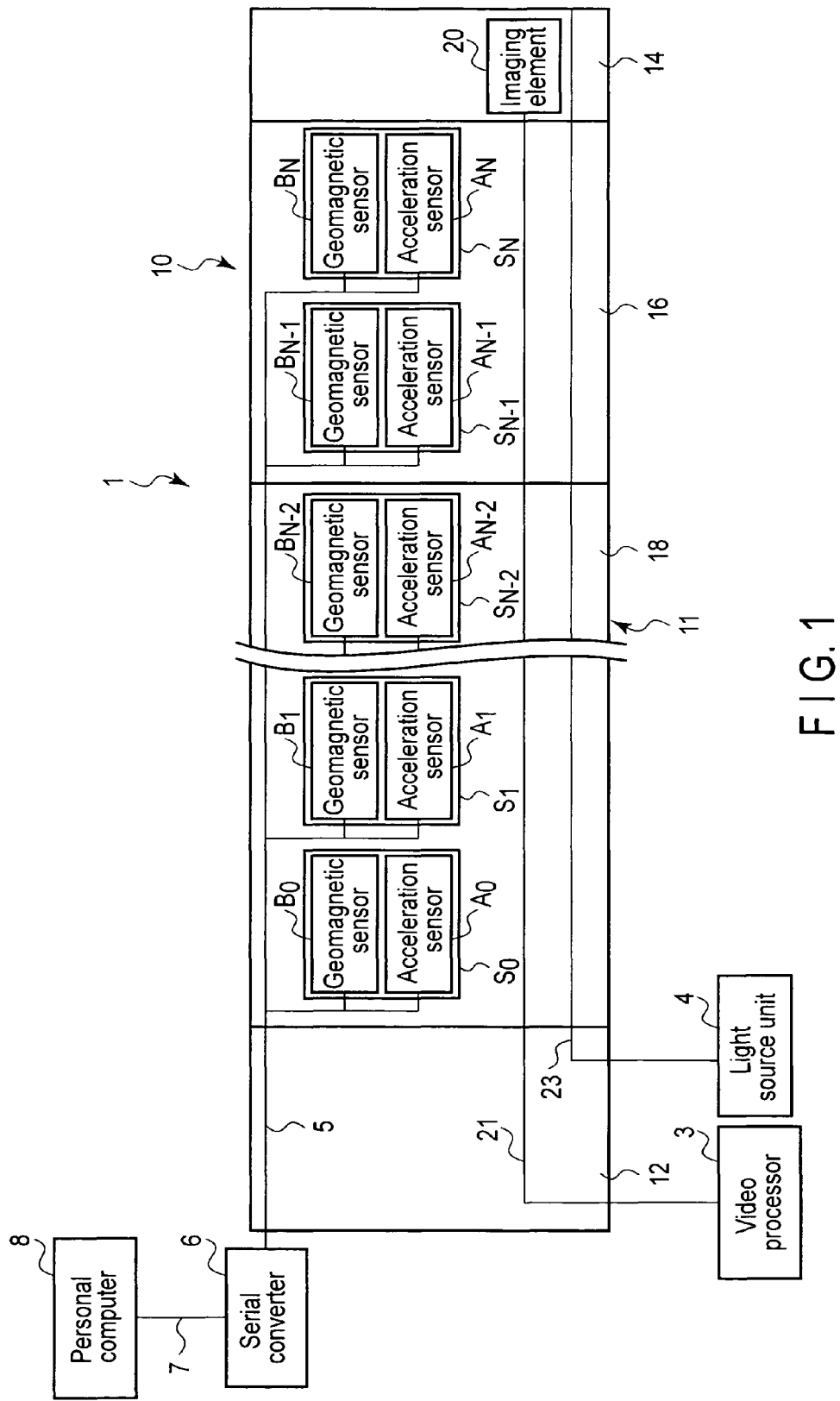
F I G. 1

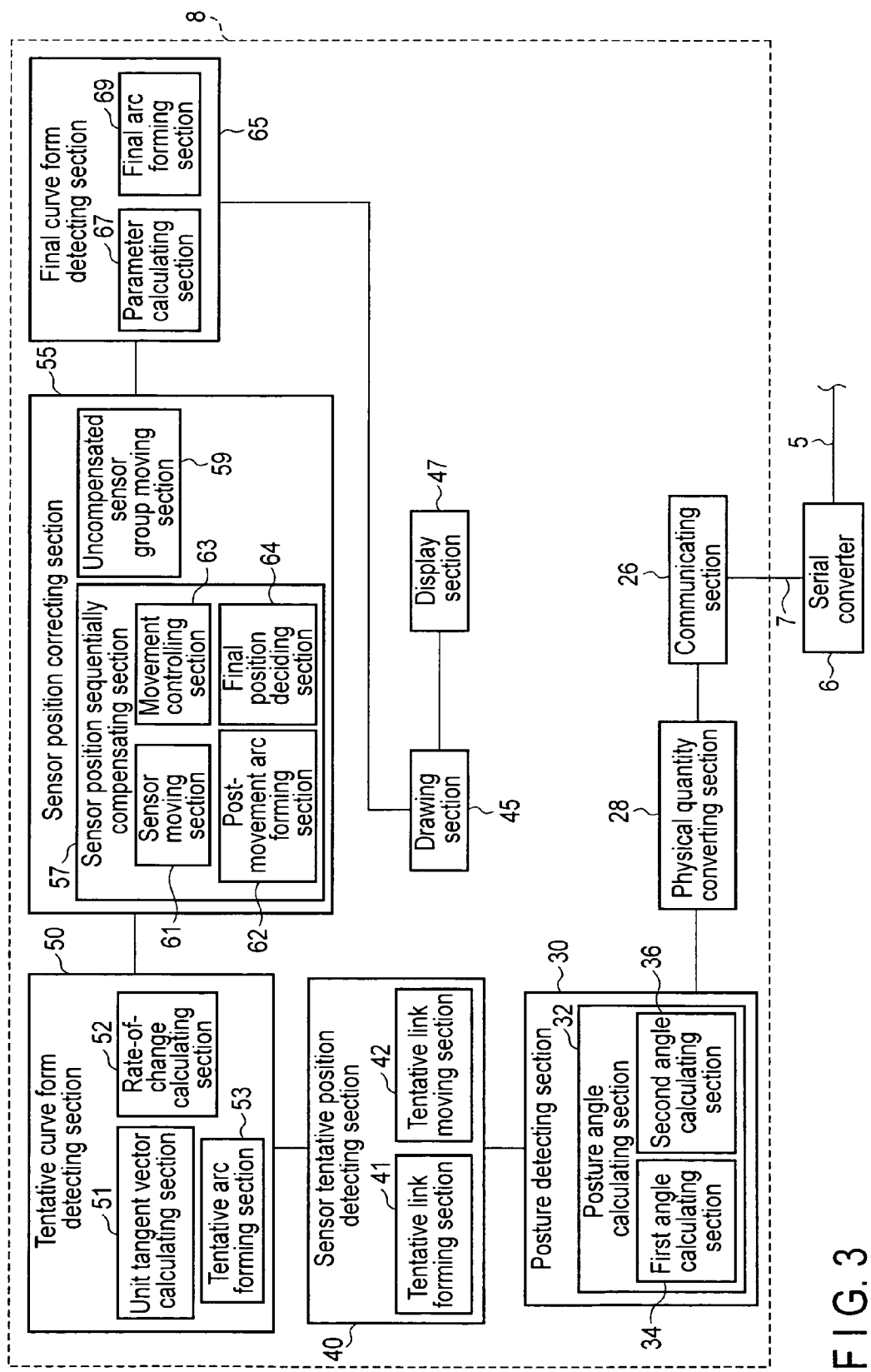
F I G. 3

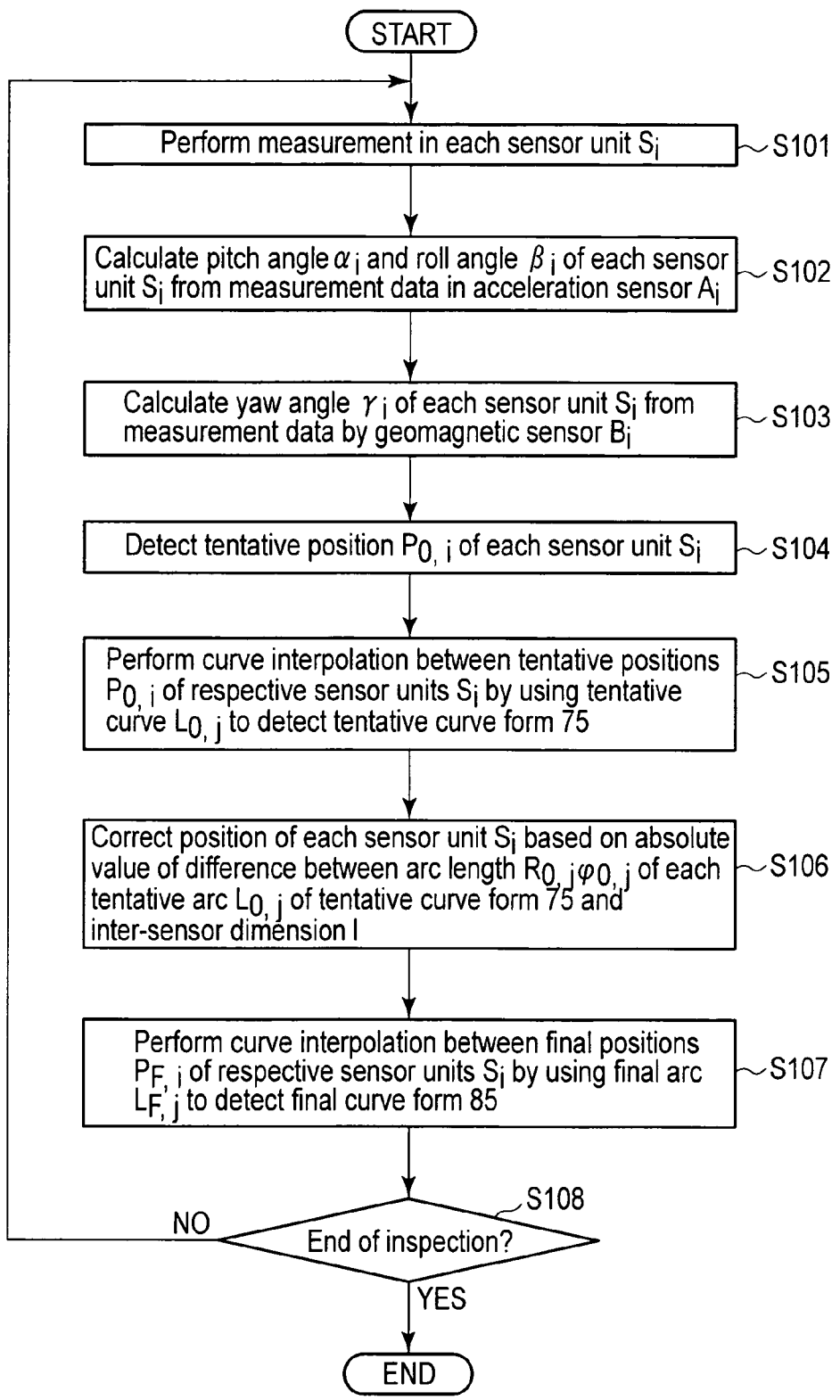
F I G. 4

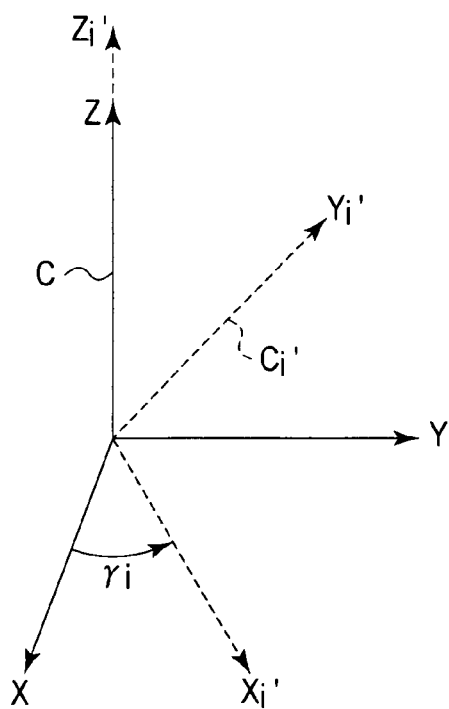
F I G. 5
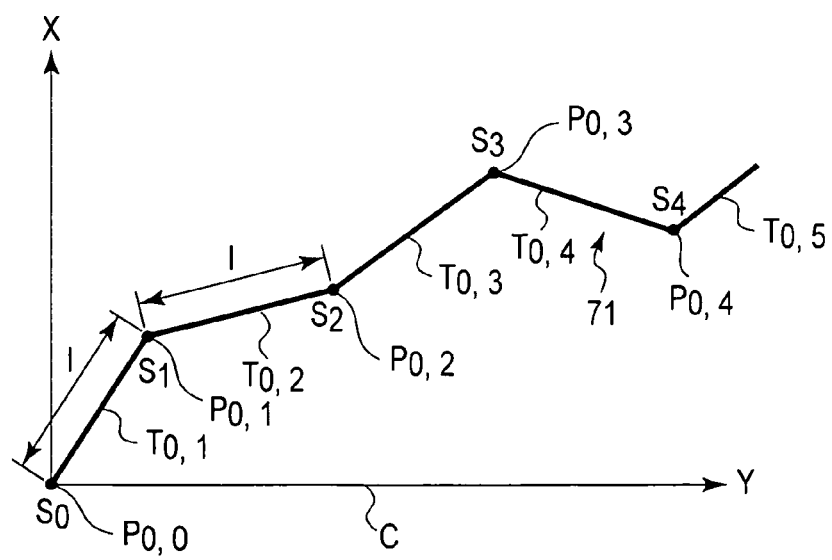
F I G. 6

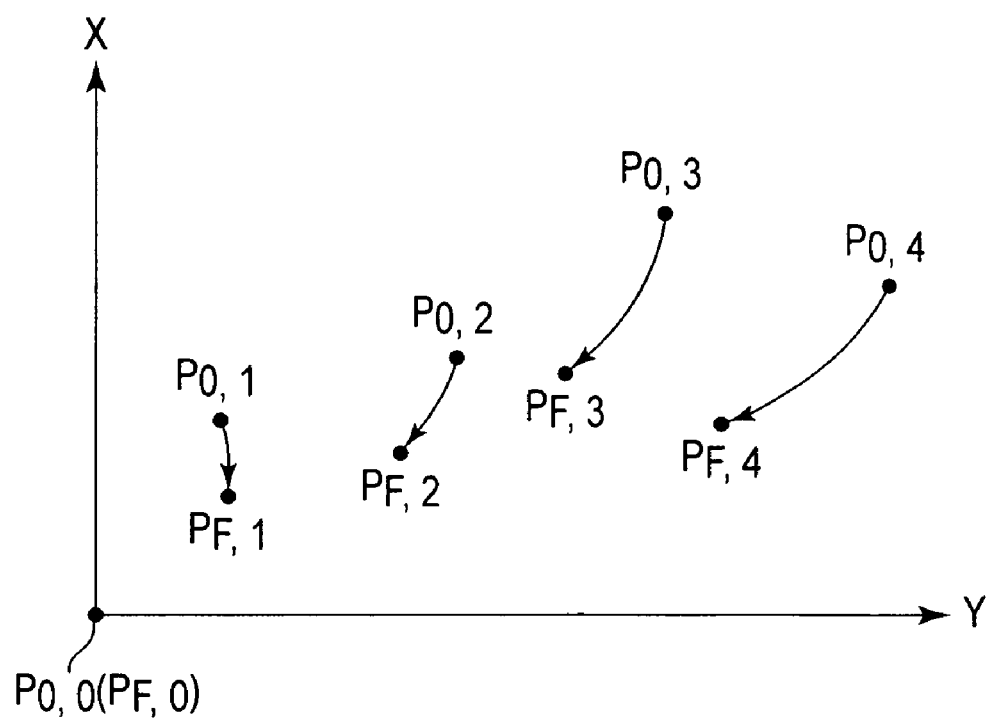
F I G. 11

US 8,403,829 B2

ENDOSCOPIC FORM DETECTION DEVICE AND FORM DETECTING METHOD OF INSERTION SECTION OF ENDOSCOPE

CROSS REFERENCE TO RELATED APPLICATIONS

This application is a Continuation Application of PCT Application No. PCT/JP2011/063736, filed Jun. 15, 2011 and based upon and claiming the benefit of priority from prior Japanese Patent Application No. 2010-191350, filed Aug. 27, 2010, the entire contents of all of which are incorporated herein by reference.

BACKGROUND OF THE INVENTION

1. Field of the Invention

The present invention relates to an endoscopic form detection device including an endoscope configured to be inserted into a body cavity and a form detecting method of an inserting section of the endoscope.

2. Description of the Related Art

In recent years, an endoscopic form detection device that can detect a form of an inserting section of an endoscope has been put to practical use. Jpn. Pat. Appln. KOKAI Publication No. 2000-175862 discloses an endoscope insertion form detection device including source coils disposed to an inserting section of an endoscope configured to be inserted into a body cavity. In this endoscope insertion form detection device, positions of the respective source coils are detected by a sense coil provided outside a body. Further, based on the detected positions of the source coils, a form of the inserting section of the endoscope is detected.

Further, Jpn. Pat. Appln. KOKAI Publication No. 2007-130175 discloses an endoscopic form detection device that configured to detect a position of each coil arranged in an inserting section of an endoscope from an alternating-current magnetic field and to perform curve interpolation with respect to a portion between the detected positions of the respective coils. In this endoscopic form detection device, the detected positions of the respective coils are connected through a Bezier curve or a spline curve to effect the curve interpolation. Performing the curve interpolation enables detecting a curve form of the inserting section of the endoscope.

BRIEF SUMMARY OF THE INVENTION

According to one aspect of the invention, an endoscopic form detection device includes that an endoscope including an inserting section in which sensor units are arranged in longitudinal directions at intervals of a predetermined inter-sensor dimension; a posture detecting section configured to detect a posture of each of the sensor units based on measurement data in the sensor unit; a sensor tentative position detecting section configured to detect a tentative position of each sensor unit on the assumption that a portion between the respective sensor units is a linear tentative link whose dimension is equal to the inter-sensor dimension based on the posture of each sensor unit detected by the posture detecting section; a tentative curve form detecting section configured to perform curve interpolation between the tentative positions of the respective sensor units by using a tentative arc to detect a tentative curve form of the inserting section based on the tentative positions of the respective sensor units detected by the sensor tentative position detecting section; a sensor position correcting section configured to correct a position of each sensor unit from the tentative position to a final position based on an absolute value of a difference between an arc length of each tentative arc of the tentative curve form detected by the tentative curve form detecting section and the inter-sensor dimension; and a final curve form detecting section configured to perform curve interpolation between the final positions of the respective sensor units by using a final arc to detect a final curve form of the inserting section.

According to one another aspect of the invention, a form detecting method of an inserting section of an endoscope, includes that performing measurement by using sensor units which are arranged in an inserting section of an endoscope in longitudinal directions at intervals of a predetermined inter-sensor dimension; detecting a posture of each of the sensor units based on measurement data in the sensor unit by using a posture detecting section; detecting a tentative position of each sensor unit by using a sensor tentative position detecting section, on the assumption that a portion between the respective sensor units is a linear tentative link whose dimension is equal to the inter-sensor dimension, based on the posture of each sensor unit detected by the posture detecting section; performing curve interpolation between the tentative positions of the respective sensor units with use of a tentative arc and detecting a tentative curve form of the inserting section, by using a tentative curve form detecting section, based on the tentative positions of the respective sensor units detected by the sensor tentative position detecting section; correcting a position of each sensor unit from the tentative position to a final position, by using a sensor position correcting section, based on an absolute value of a difference between an arc length of each tentative arc of the tentative curve form detected by the tentative curve form detecting section and the inter-sensor dimension; and performing curve interpolation between the final positions of the respective sensor units with use of a final arc and detecting a final curve form of the inserting section by using a final curve form detecting section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration of an endoscopic form detection device according to a first embodiment of the present invention;

FIG. 3 is a block diagram showing a configuration of a personal computer of the endoscopic form detection device according to the first embodiment;

FIG. 4 is a flowchart showing a method of detecting a form of the inserting section of an endoscope in a stationary state according to the first embodiment;

FIG. 5 is a schematic view showing a global coordinate system and a correction coordinate system of the endoscopic form detection device according to the first embodiment in comparison with each other;

FIG. 6 is a schematic view showing tentative positions of respective sensor units detected by a sensor tentative position detecting section of the endoscopic form detection device according to the first embodiment;

FIG. 11 is a schematic view showing final positions of the respective sensor units corrected by a sensor position correcting section of the endoscopic form detection device according to the first embodiment;

DETAILED DESCRIPTION OF THE INVENTION

First Embodiment

Figure 2:
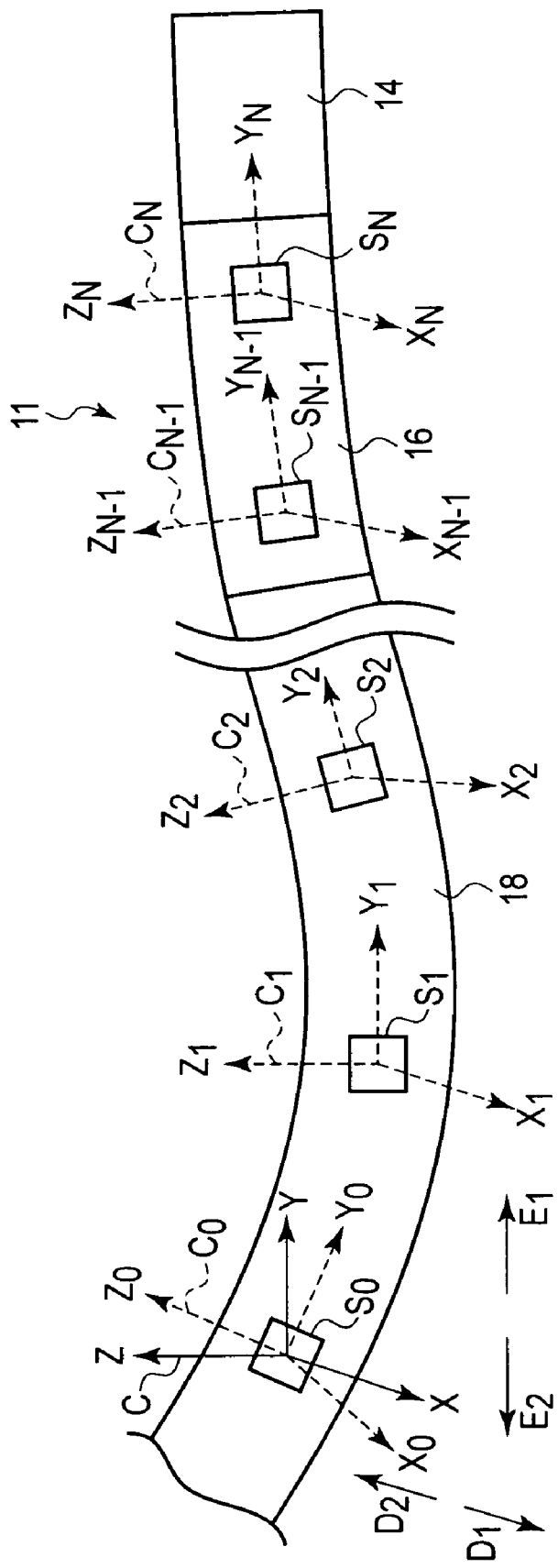
FIG. 2 is a schematic view showing a configuration of an inserting section of an endoscope according to the first embodiment.

A first embodiment according to the present invention will now be described with reference to FIG. 1 to FIG. 18.

FIG. 1 is a view showing an endoscopic form detection device 1 according to a first embodiment. As shown in FIG. 1, an endoscope 10 of the endoscopic form detection device 1 includes an inserting section 11 configured to be inserted into a body cavity and an operating section 12 provided to a proximal end side of the inserting section 11. The inserting section 11 includes a distal-end hard section 14 provided at a most distal end side; a bending section 16 provided to the proximal end side of the distal-end hard section 14, and an elongated flexible tube section 18 provided to the proximal end side of the bending section 16.

An imaging element 20 such as a CCD configured to image a subject is provided in the distal-end hard section 14. One end of an imaging signal line 21 is connected to the imaging element 20. The imaging signal line 21 is extended to the outside of the endoscope 10 from the operating section 12 through the inserting section 11, and the other end of the imaging signal line 21 is connected to a video processor 3 which is an image processing unit. Furthermore, a light guide 23 configured to guide illumination light applied to a subject is extended to an illumination window (not shown) of the distal-end hard section 14 along longitudinal directions in the inserting section 11. The light guide 23 is extended to the outside of the endoscope 10 from the operating section 12 and connected to a light source unit 4.

Moreover, one end of each of four bending operation wires (not shown) as bending operation transmission members is connected to a distal end portion of the bending section 16 in the inserting section 11. The other end of each bending operation wire is connected to a bending operation knob (not shown), which is a bending operating section provided to the operating section 12, through the flexible tube section 18. The bending operation wires move in the longitudinal directions by operations using the bending operation knob. The bending section 16 is configured to bend in up-down directions and left-right directions of the endoscope 10 by the movement of the bending operation wires.

A plurality of (N+1 in this embodiment) sensor units $S_0$ to $S_N$ are provided in the inserting section 2. The respective sensor units $S_i$ (i=0, 1, 2, . . . , N) are arranged to be apart from each other in the longitudinal directions at fixed intervals (=50 mm). That is, respective sensor units $S_i$ are arranged to be apart from each other in the longitudinal directions at intervals of a predetermined inter-sensor dimension l. Here, for example, the sensor unit $S_0$ provided on a most proximal end side is arranged in a proximal end portion of the flexible tube section 18, and the sensor unit $S_N$ provided on the most distal end side is arranged in the distal end portion of the bending section 16. Each sensor unit $S_i$ includes an accelerator sensor $A_i$ configured to measure acceleration, and a geomagnetic sensor $B_i$ configured to measure earth magnetism.

FIG. 2 is a view showing the inserting section 11 of the endoscope 10. As shown in FIG. 2, each sensor unit $S_i$ has a local coordinate system $C_i$ (indicated by a dotted line in FIG. 2) having an origin at the center of the sensor unit $S_i$, and also having an $X_i$ axis, a $Y_i$ axis, and a $Z_i$ axis. Here, the $X_i$ axis directions coincide with the left-right directions of the endoscope 10 at the center of the sensor unit $S_i$, and a right direction of the endoscope 10 as seen from the proximal end side is determined to be positive. The $Y_i$ axis directions coincide with the longitudinal directions at the center of the sensor unit $S_i$, and the distal end side direction is determined to be positive. The $Z_i$ axis directions coincide with the up-down directions of the endoscope 10 at the center of the sensor unit $S_i$, and an up direction of the endoscope 10 is determined to be positive. The acceleration sensor $A_i$ is configured to measure an $X_i$ axis directions component, a $Y_i$ axis directions component, and a $Z_i$ axis directions component of acceleration at the origin of the local coordinate system $C_i$.

Furthermore, in the endoscopic form detection device 1, a global coordinate system C (indicated by a solid line in FIG. 2) having an X axis, a Y axis, and a Z axis is defined with the center of the sensor unit $S_0$ provided on the most proximal end side being determined as an origin. Here, the global coordinate system C is a rectangular Cartesian coordinate system for a right-hand system with the center of the sensor unit $S_0$ provided on the most proximal end side determined as an origin. The X-axis directions coincide with predetermined directions (directions parallel to arrows D1 and D2 in FIG. 2 in this embodiment) perpendicular to vertical directions in which gravity functions, and a direction of the arrow D1 in FIG. 2 is determined to be positive. The Y axis directions coincide with directions (directions parallel to arrows E1 and E2 in FIG. 2 in this embodiment) perpendicular to the vertical directions and the X axis directions, and a direction of the arrow E1 in FIG. 2 is determined to be positive. The Z axis directions coincide with the vertical directions, and an up direction (direction extending from a back side to a front side of a paper sheet) of the vertical directions is determined to be positive. It is to be noted that a positive direction of the X axis directions of the global coordinate system is determined as a magnetic north direction for convenience of explanation.

Each local coordinate system $C_i$ is a coordinate system obtained by rotating the global coordinate system C $\alpha_i$ about the X axis, $\beta_i$ about the Y axis, and $\gamma_i$ about the Z axis and parallel translating the origin from the center of the sensor unit $S_0$ provided on the most proximal end side to the center of the sensor unit $S_i$. Here, $\alpha_i$ is referred to as a pitch angle, $\beta_i$ is referred to as a roll angle, $\gamma_i$ is referred to as a yaw angle, and three angles, i.e., the pitch angle $\alpha_i$, the roll angle $\beta_i$, and the yaw angle $\gamma_i$ will be generically referred to as posture angles. A clockwise direction of each posture angle $\alpha_i$, $\beta_i$, or $\gamma_i$ seen from a negative direction of each of the X axis, the Y axis, and the Z axis is determined to be positive. A posture of the sensor unit $S_i$ can be detected by calculating values of the posture angles $\alpha_i$, $\beta_i$, and $\gamma_i$.

As shown in FIG. 1, a serial bus 5 such as I2C is connected to the acceleration sensor $A_i$ and the geomagnetic sensor $B_i$ of each sensor unit $S_i$. The serial bus 5 is extended to the outside of the endoscope 10 from the operating section 12 through the inside of the inserting section 11, and its proximal end is connected to a serial converter 6. The serial converter 6 is configured to convert a serial signal of measurement data input from each sensor unit $S_i$ through the serial bus 5 into a USB signal. One end of a USB cable 7 is connected to the serial converter 6. The other end of the USB cable 7 is connected to a personal computer 8. The USB signal of the measurement data in each sensor unit $S_i$ is configured to be input to the personal computer 8 from the serial converter 6.

FIG. 3 is a view showing a configuration of the personal computer 8. As shown in FIG. 3, the personal computer 8 includes a communicating section 26 connected to the serial converter 6 through the USB cable 7. The communicating section 26 is configured to receive the measurement data in each sensor unit $S_i$. A physical quantity converting section 28 is connected to the communicating section 26. The physical quantity converting section 28 is configured to convert the measurement data in each sensor unit $S_i$ received by a communicating section 26 into a physical quantity by using an offset, a gain, and others.

A posture detecting section 30 is connected to the physical quantity converting section 28. The posture detecting section 30 is configured to detect a posture of each sensor unit $S_i$ based on the measurement data in each sensor unit $S_i$. The posture detecting section 30 includes a posture angle calculating section 32 configured to calculate the three posture angles $\alpha_i$, $\beta_i$, and $\gamma_i$ as rotational angles in the local coordinate system $C_i$ of each sensor unit $S_i$ about the X axis, the Y axis, and the Z axis from the global coordinate system C based on measurement data obtained by the acceleration sensor $A_i$ and the geomagnetic sensor $B_i$ of each sensor unit $S_i$. The posture angle calculating section 32 includes a first angle calculating section 34 configured to calculate a pitch angle $\alpha_i$ as a rotational angle in the local coordinate system $C_i$ of each sensor unit $S_i$ about the X axis from the global coordinate system C and a roll angle $\beta_i$ as a rotational angle in the local coordinate system $C_i$ of each sensor unit $S_i$ about the Y axis from the global coordinate system C based on measurement data in the acceleration sensor $A_i$ and the geomagnetic sensor Bi of each sensor unit $S_i$. Moreover, the posture angle calculating section 32 also includes a second angle calculating section 36 configured to calculate a yaw angle $\gamma_i$ as a rotational angle in the local coordinate system $C_i$ of each sensor unit $S_i$ about the Z axis from the global coordinate system C based on the geomagnetic data in the geomagnetic sensor $B_i$ of each sensor unit $S_i$.

A method of detecting a posture of each sensor unit $S_i$ by the posture detecting section 30 will now be described. FIG. 4 is a flowchart showing a form detecting method of the inserting section 11 in a stationary state in which the inserting section 11 of the endoscope 10 is stopped. As shown in FIG. 4, when detecting a form of the inserting section 11, each sensor unit $S_i$ first performs measurement (a step S101), and the posture detecting section 30 acquires measurement data in each sensor unit $S_i$. Additionally, the posture angle calculating section 32 calculates the three posture angles $\alpha_i$, $\beta_i$, and $\gamma_i$ in the local coordinate system $C_i$ of each sensor unit $S_i$.

When calculating the posture angles $\alpha_i$, $\beta_i$, and $\gamma_i$, the first angle calculating section 34 first calculates the pitch angle $\alpha_i$ and the roll angle $\beta_i$ in the local coordinate system $C_i$ of each sensor unit $S_i$ (a step S102) based on the measurement data in the acceleration sensor $A_i$ of each sensor unit $S_i$. Here, the posture angles $\alpha_i$, $\beta_i$, and $\gamma_i$ are determined as a (Z, X, Y) type that rotates in the order of the yaw angle $\gamma_i$, the pitch angle $\alpha_i$, and the roll angle $\beta_i$. Therefore, a rotation matrix from the global coordinate system C to the local coordinate system $C_i$ is as follows:

$$C_{Bi}^{G} = R_{Zi} R_{Xi} R_{Yi} \quad (1)$$

$$= \begin{bmatrix} \cos\gamma_i & -\sin\gamma_i & 0 \\ \sin\gamma_i & \cos\gamma_i & 0 \\ 0 & 0 & 1 \end{bmatrix} \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix}$$

$$= \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_i \cdot \sin\beta_i + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_i & \sin\alpha_i & \cos\alpha_i \cdot \cos\beta_i \end{bmatrix}$$

In the stationary state in which the inserting section 11 is stopped, gravitational acceleration alone functions downward in the vertical directions. That is, in both the global coordinate system C and the local coordinate system $C_i$, the gravitational acceleration alone functions downward in the vertical directions. Therefore, at this time, an X axis directions component, a Y axis directions component, and a Z axis directions component of an acceleration vector in the global coordinate system C are as follows:

$$\dot{a}_{th} = [0\ 0\ -g]^T \quad (2)$$

Further, it is assumed that an $X_i$ axis directions component, a $Y_i$ axis directions component, and a $Z_i$ axis directions component of an acceleration vector in the local coordinate system $C_i$ measured by the acceleration sensor Ai are as follows:

$$\dot{a}_{obsi} = [a_{Bi\_X} a_{Bi\_Y} a_{Bi\_Z}]^T \quad (3)$$

Here, the local coordinate system $C_i$ is a coordinate system obtained by rotating the global coordinate system C in the order of the yaw angle $\gamma_i$, the pitch angle $\alpha_i$, and the roll angle $\beta_i$. Therefore, based on Expression (1) to Expression (3), acceleration components observed in the local coordinate system $C_i$ are as follows:

$$\dot{a}_{obsi} = (C_{Bi}^G)^T \dot{a}_{th} = -g \begin{bmatrix} -\cos\alpha_i \cdot \sin\beta_i \\ \sin\alpha_i \\ \cos\alpha_i \cdot \cos\beta_i \end{bmatrix} \begin{matrix} (4.1) \\ (4.2) \\ (4.3) \end{matrix}$$

Here, when a square of Expression (4.1) is added to a square of Expression (4.2), the following expression can be obtained:

$$a_{Bi\_X}^2 + a_{Bi\_Z}^2 = g^2 \cos^2\alpha_i(\sin^2\beta_i + \cos^2\beta_i) \quad (5)$$

Further, the following expression is derived:

$$g\cos\alpha_i = \sqrt{a_{Bi\_X}^2 + a_{Bi\_Z}^2} \quad (6)$$

Furthermore, when Expression (4.2) is divided by Expression (6), the following expression can be obtained:

$$\alpha_i = \tan^{-1}\left(\frac{-a_{Bi\_Y}}{\sqrt{a_{Bi\_X^2} + a_{Bi\_Z^2}}}\right) \quad (7)$$

As a result, the pitch angle $\alpha_i$ in the local coordinate system $C_i$ can be obtained. Moreover, when Expression (4.1) is divided by Expression (4.3), the following expression can be obtained:

$$\beta_i = \tan^{-1}\left(-\frac{a_{Bi\_X}}{a_{Bi\_Z}}\right) \quad (8)$$

The roll angle $\beta_i$ in the local coordinate system $C_i$ can be derived. As described above, based on measurement data in each acceleration sensor $A_i$, the pitch angle $\alpha_i$ and the roll angle $\beta_i$ in the local coordinate system $C_i$ can be calculated.

Additionally, the second angle calculating section 36 calculates the yaw angle $\gamma_i$ in the local coordinate system $C_i$ of each sensor unit Si based on measurement data obtained by the geomagnetic sensor $B_i$ of each sensor unit $S_i$ (a step S103). Here, a corrected coordinate system $C'_i$ obtained by correcting the rotation from the global coordinate system C about the X axis and the rotation from the global coordinate system C about the Y axis in each local coordinate system $C_i$ is defined by using the pitch angle $\alpha_i$ and the roll angle $\beta_i$ calculated at the step S102. FIG. 5 is a view showing the global coordinate system C (indicated by a solid line in FIG. 5) and the corrected coordinate system $C'_i$ (indicated by a dotted line in FIG. 5). It is to be noted that the global coordinate system C and the corrected coordinate system $C'_i$ actually have origins provided at different positions, and FIG. 5 shows a state in which the origins are provided at the same position in order to compare both the coordinate systems. As shown in FIG. 5, the corrected coordinate system $C'_i$ obtained by correcting the rotation about the X axis and the rotation about the Y axis is a coordinate system obtained by rotating the global coordinate system C by the yaw angle $\gamma_i$ about the Z axis and has an $X'_i$ axis, a $Y'_i$ axis, and a $Z'_i$ axis. $X'_i$ directions and $Y'_i$ axis directions coincide with directions rotated by the yaw angle $\gamma i$ about the Z axis from the X axis directions and the Y axis directions in the global coordinate system C, respectively. $Z'_i$ axis directions coincide with the vertical directions, i.e., the Z axis directions in the global coordinate system C. Here, since the positive direction of the X axis directions in the global coordinate system C coincides with the magnetic north direction, a positive direction of the $X'_i$ directions is a direction rotated by the yaw angle $\gamma_i$ about the Z axis from the magnetic north direction.

It is assumed that an $X_i$ axis directions component, a $Y_i$ axis directions component, and a $Z_i$ axis directions component of a geomagnetic vector in the local coordinate system $C_i$ measured by the geomagnetic sensor $B_i$ are as follows:

$$\dot{m}_{obsi} = [M_{Xi} M_{Yi} M_{Zi}]^T \quad (9)$$

The corrected coordinate system $C'_i$ is a coordinate system obtained by correcting the rotation from the global coordinate system C about the X axis and the rotation from the global coordinate system C about the Y axis in the local coordinate system $C_i$. Therefore, based on $R_{xi}$ and $R_{yi}$ in Expression (1) and Expression (9), an $X'_i$ axis directions component, a $Y'i$ axis directions component, and a $Z'_i$ axis directions component in the corrected coordinate system $C'_i$ of a geomagnetic vector measured by the geomagnetic sensor $B_i$ are as follows:

$$\dot{m}'_{obsi} = R_{Xi} R_{Yi} \dot{m}_{obsi} \quad (10.1)$$

$$= \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix} \begin{bmatrix} M_{Xi} \\ M_{Yi} \\ M_{Zi} \end{bmatrix}$$

$$= \begin{bmatrix} \cos\beta_i & 0 & \sin\beta_i \\ \sin\alpha_i\sin\beta_i & \cos\alpha_i & -\sin\alpha_i\cos\beta_i \\ -\cos\alpha_i\sin\beta_i & \sin\alpha_i & \cos\alpha_i\cos\beta_i \end{bmatrix} \begin{bmatrix} M_{Xi} \\ M_{Yi} \\ M_{Zi} \end{bmatrix}$$

$$\dot{m}'_{obsi} = [M'_{Xi}\ M'_{Yi}\ M'_{Zi}]^T \quad (10.2)$$

Based on Expression (10.1) and Expression (10.2), the following expressions can be obtained:

$$M_{Xi}' = M_{Xi}\cos\beta_i + M_{Zi}\sin\beta_i \quad (11.1)$$

$$M_{Yi}' = M_{Yi}\cos\alpha_i + \sin\alpha_i(M_{Xi}\sin\beta_i - M_{Zi}\cos\beta_i) \quad (11.2)$$

A geomagnetic component on a horizontal plane (an $X'_i$–$Y'_i$ plane in the corrected coordinate system $C'_i$) perpendicular to the vertical directions directs the magnetic north direction. Therefore, based on Expression (11.2) and Expression (11.2), an angle $\theta_i$ from the $X'_i$ axis to the magnetic north direction can be obtained by using the $X'_i$ axis component and the $Y'_i$ axis component of the geomagnetic vector in the corrected coordinate system $C'_i$. That is, the following expression can be obtained:

$$\theta_i = \tan^{-1}(M'_{Yi}/M'_{Xi}) \quad (12)$$

In regard to the angle $\theta_i$, a clockwise direction when seeing the $Z'_i$ axis (the Z axis) from a negative direction is determined to be positive. Here, the corrected coordinate system $C'_i$ is a coordinate system obtained by rotating the global coordinate system C the yaw angle $\gamma_i$ about the Z axis. Therefore, the angle $\theta_i$ obtained based on Expression (12) is the yaw angle $\gamma_i$ in the local coordinate system $C_i$ when the global coordinate system C is determined as a reference.

It is to be noted that, when one of the X axis directions in the global coordinate system C does not coincide with the magnetic north direction, the yaw angle $\gamma_i$ can be likewise obtained with reference to the magnetic north. An X axis directions component, a Y axis directions component, and a Z axis directions component of the geomagnetic vector in the global coordinate system C are determined as follows:

$$\dot{m}_{th} = [E_X E_Y E_Z]^T \quad (13)$$

The X axis directions component, the Y axis directions component, and the Z axis directions component of the geomagnetic vector in the global coordinate system C can be obtained by using a geomagnetic sensor which is of the same type as the geomagnetic sensor $B_i$ to conduct the measurement in a state in which the X axis directions, the Y axis directions, and the Z axis directions in the global coordinate system C coincide with axis directions. Further, based on Expression (13), an angle $\theta$ from the X axis to the magnetic north direction is obtained by using the X axis component and the Y axis component of the geomagnetic vector in the global coordinate system C. That is, the following expression can be acquired:

$$\theta = \tan^{-1}(E_Y/E_X) \quad (14)$$

Here, in regard to the angle $\theta$, the clockwise direction when the Z axis is seen from the negative direction is determined to be positive. The corrected coordinate system $C'_i$ is a coordinate system obtained by rotating the global coordinate system C by the yaw angle $\gamma_i$ about the Z axis. Therefore, based on Expression (12) and Expression (14), the following representation can be achieved:

$$\gamma_i = \theta - \theta_i \quad (15)$$

As a result, when the global coordinate system C is determined as a reference the yaw angle $\gamma_i$ of the local coordinate system $C_i$ can be obtained.

As described above, based on the measurement data in each geomagnetic sensor $B_i$, the yaw angle $\gamma_i$ of each local coordinate system $C_i$ is calculated. Based on the calculated values of the posture angles $\alpha_i$, $\beta_i$, and $\gamma_i$, the posture detecting section 30 is configured to detect a posture of each sensor unit $S_i$.

As shown in FIG. 3, a sensor tentative position detecting section 40 is connected to the posture detecting section 30. FIG. 6 is a view showing tentative positions $P_{0,i}$ of respective sensor units $S_i$ detected by the sensor tentative position detecting section 40 from a negative direction toward a positive direction of the global coordinate system C. As shown in FIG. 6, the sensor tentative position detecting section 40 is configured to detect the tentative position $P_{0,i}$ of each sensor unit $S_i$ on the assumption that a form between the respective sensor units $S_i$ is a linear tentative link $T_{0,j}$ (j=1, 2, ... N) equal to the inter-sensor dimension l based on a posture of each sensor unit $S_i$ detected by the posture detecting section 30. Here, a kth tentative link $T_{0,k}$ from the proximal end side is a tentative link $T_{0,k}$ between a kth sensor unit $S_{k-1}$ from the proximal end side and a (k+1)th sensor unit $S_k$ from the proximal end side. The sensor tentative position detecting section 40 includes a tentative link forming section 41 configured to form each tentative link $T_{0,j}$, and a tentative link moving section 42 configured to parallel translate each tentative link $T_{0,j}$ formed by each tentative link forming section 41. The tentative link forming section 42 is configured to parallel translate each tentative link $T_{0,j}$ in such a manner that tentative link boundaries between each tentative link $T_{0,j}$ and adjacent tentative links $T_{0,j-1}$ and $T_{0,j+1}$ become continuous. As a result, a tentative linear form 71 is formed on the assumption that a form between the respective sensor units $S_i$ is a linear tentative link $T_{0,j}$.

Here, a method of detecting the tentative position $P_{0,i}$ of each sensor unit $S_i$ by the sensor tentative position detecting section 40 will now be described. When detecting the tentative position $P_{0,i}$ of each sensor unit $S_i$ (a step S104), the tentative link forming section 41 is configured to first form each tentative link $T_{0,j}$ having a linear form based on values of the posture angles $\alpha_i$, $\beta_i$, and $\gamma_i$ calculated at the steps S102 and S103. Here, description will be given as to the formation of the kth tentative link $T_{0,k}$ from the proximal end side between the kth sensor unit $S_{k-1}$ from the proximal end side and the (k+1)th sensor unit $S_k$ from the proximal end side.

Posture angles $\alpha_{k-1}$, $\beta_{k-1}$, and $\gamma_{k-1}$ in a local coordinate system $C_{k-1}$ (i.e., the tentative link $T_{0,k}$) are calculated at the steps S102 and 103 by using expressions obtained by substituting i in Expression (7), Expression (8), and Expression (12) (or Expression (15)) by k−1. A vector extending from the sensor unit $S_{k-1}$ toward the sensor unit $S_k$ is obtained by using the posture angles $\alpha_{k-1}$, $\beta_{k-1}$, and $\gamma_{k-1}$ and the inter-sensor dimension l which is an interval between respective sensor units $S_i$. Here, the vector extending from the sensor unit $S_{k-1}$ toward the sensor unit $S_k$ is represented as follows:

$$\begin{aligned}
l_k &= [l_{xk} \quad l_{yk} \quad l_{zk}]^T \\
&= lC^G_{Bk-1}\hat{f}_{yk-1} \\
&= l\begin{bmatrix} -\sin\gamma_{k-1} \cdot \cos\alpha_{k-1} \\ \cos\gamma_{k-1} \cdot \cos\alpha_{k-1} \\ \sin\alpha_{k-1} \end{bmatrix}
\end{aligned} \quad (16.1)$$

$$\hat{f}_{yk-1} = [0 \quad 1 \quad 0]^T \quad (16.2)$$

In Expression (16.1), components obtained by dividing a unit vector in a $Y_{k-1}$ axis directions at the origin of the local coordinate system $C_{k-1}$ into an X axis directions component, a Y axis directions component, and a Z axis directions component in the global coordinate system C are calculated by multiplying the unit vector in the $Y_{k-1}$ axis directions at the origin of the local coordinate system $C_{k-1}$ by a rotation matrix calculated by Expression (1). That is, $l_{xk}$, $l_{yk}$, and $l_{zk}$ are components obtained by dividing a vector having a magnitude l in the $Y_{k-1}$ axis directions in the local coordinate system $C_{k-1}$ to the X axis directions, the Y axis directions, and the Z axis directions in the global coordinate C. The tentative link $T_{0,k}$ is formed by each vector calculated based on Expression (16.1).

It is to be noted each tentative link $T_{0,j}$ other than the tentative link $T_{0,k}$ is likewise formed by the tentative link forming section 41. That is, a vector from the sensor unit $S_{j-1}$ on the proximal end side (a side close to the origin of the global coordinate system C) of the tentative link $T_{0,j}$ to the sensor unit $S_j$ on the distal end side (a side far from the origin of the global coordinate system C) of the tentative link $T_{0,j}$ is obtained. Further, the tentative link $T_{0,j}$ is formed by using the vector from the sensor unit $S_{j-1}$ to the sensor unit $S_j$. That is, the tentative link forming section 41 is configured to form the tentative link $T_{0,j}$ on the assumption that the tentative link $T_{0,j}$ is extended from the center of the sensor unit $S_{j-1}$ on the proximal end side (the side close to the origin of the global coordinate system C) to the center of the sensor unit $S_j$ on the distal end side (the side far from the origin of the global coordinate system C) in longitudinal directions at the center of the sensor unit $S_{j-1}$ on the proximal end side.

Further, it is preferable for the inter-sensor dimension l to be approximately 50 mm. Increasing the inter-sensor dimension l enables reducing the number of the sensor units $S_i$ and also decreasing a cost. Furthermore, when the inter-sensor dimension l is smaller than approximately 50 mm, errors when detecting a form of the inserting section 11 can be reduced even if a form between the respective sensor units $S_i$ is assumed to be the linear tentative link $T_{0,j}$ whose dimension is equal to the inter-sensor dimension l.

Figure 7:
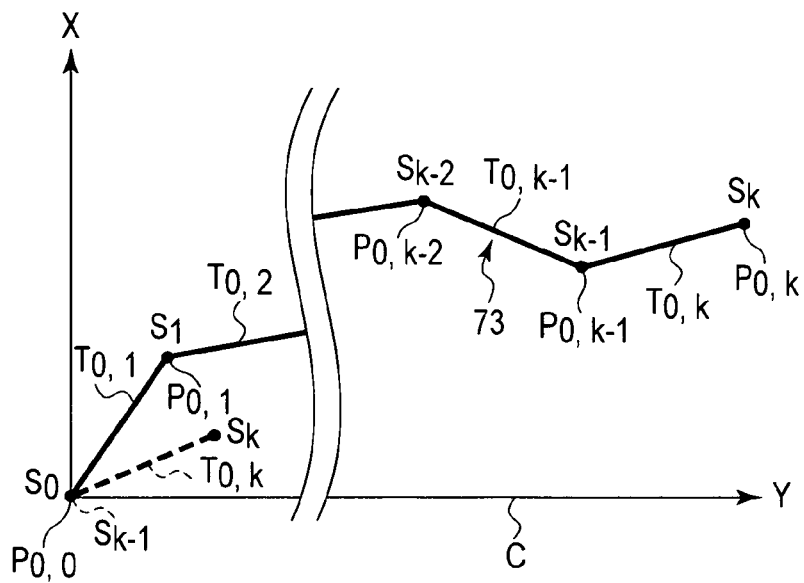
FIG. 7 is a schematic view explaining processing in a tentative link moving section of the sensor tentative position detecting section according to the first embodiment.

Moreover, the tentative link moving section 42 is configured to parallel translate each tentative link $T_{0,j}$ formed by the tentative link forming section 41 in such a manner that tentative link boundaries between each tentative link $T_{0,j}$ and adjacent tentative likes $T_{0,j-1}$ and $T_{0,j+1}$ become continuous. FIG. 7 is a view explaining processing in the tentative link moving section 42. Here, description will be given as to movement of the kth tentative link $T_{0,k}$ from the proximal end side between the kth sensor unit $S_{k-1}$ from the proximal end side and the (k+1)th sensor unit $S_k$ from the proximal end side.

As shown in FIG. 7, in a state before the tentative link $T_{0,k}$ is moved by the tentative link moving section 42, the movement from a first tentative link to the tentative link $T_{0,k-1}$ adjacent to the proximal end side of the tentative link $T_{0,k}$ is completed, and a tentative link movement completed portion 73 is formed. When moving the tentative link $T_{0,k}$, the tentative link moving section 42 is configured to parallel translate the tentative link $T_{0,k}$ a distance from the origin to a distal end of the tentative link movement completed portion 73 (i.e., a tentative position $P_{0,k-1}$ of the sensor unit $S_{k-1}$). That is, the tentative link $T_{0,k}$ is parallel translated from a position indicated by a dotted line in FIG. 7 to a position indicated by a solid line in FIG. 7. As a result, a boundary between the tentative link $T_{0,k-1}$ and the tentative link $T_{0,k}$ becomes continuous.

It is to be noted that the tentative link moving section 42 likewise moves each tentative link $T_{0,j}$ other than the tentative link $T_{0,k}$. That is, when moving the tentative link $T_{0,j}$, the tentative link moving section 42 is configured to parallel translate the tentative link $T_{0,j}$ a distance from the origin to the distal end of the tentative link movement completed portion 73 (an end on the side far from the origin in the global coordinate system C). As a result, a tentative link boundary between the tentative link $T_{0,j}$ and a tentative link $T_{0,j-1}$ adjacent to a proximal end side (the side close to the origin in the global coordinate system C) of the tentative link $T_{0,j}$ becomes continuous. However, in regard to the tentative link $T_{0,1}$, since a proximal end of the tentative link $T_{0,1}$ is the origin in the global coordinate system C, the movement is not carried out. When the movement of all the tentative links $T_{0,j}$ is completed, the tentative linear form 71 is formed on the assumption that a form between the respective sensor units $S_i$ is the linear tentative link $T_{0,j}$, as shown in FIG. 6. Positions of the respective sensor units $S_i$ in the tentative linear form 71 are detected as tentative positions $P_{0,i}$ of the respective sensor units $S_i$ (the step S104).

Figure 8:
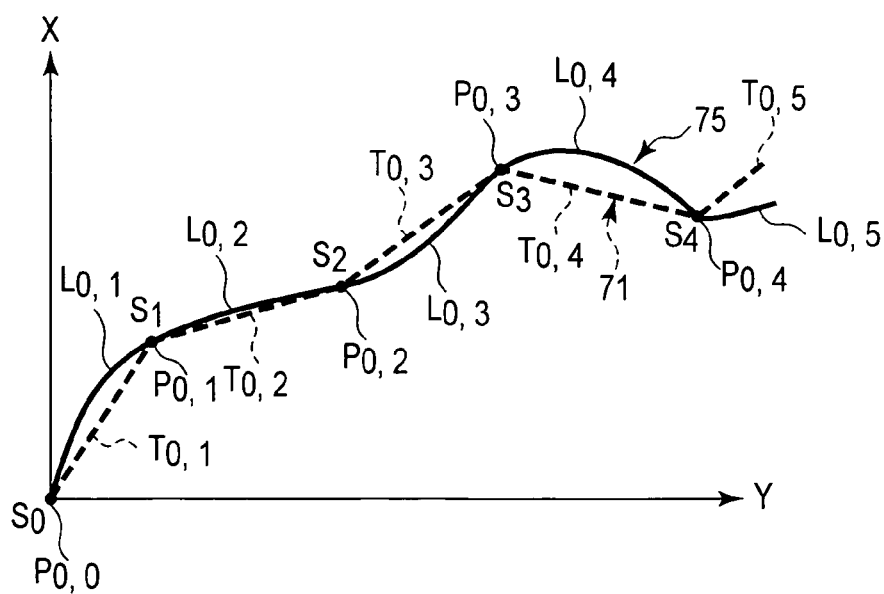
FIG. 8 is a schematic view showing a tentative curve form of the inserting section of an endoscope detected by a tentative curve form detecting section of the endoscopic form detection device according to the first embodiment.

As shown in FIG. 3, the sensor tentative position detecting section 40 is connected to a tentative curve form detecting section 50. The tentative curve form detecting section 50 is configured to perform curve interpolation on the assumption that a form between tentative positions $P_{0,i}$ of the respective sensor units $S_i$ detected by the sensor tentative position detecting section 40 is a tentative arc $L_{0,j}$, thereby detecting a tentative curve form 75. FIG. 8 is a view showing the tentative curve form 75 of the inserting section 11 of the endoscope 10 detected by the tentative curve form detecting section 50 from the negative direction toward the positive direction of the Z axis in the global coordinate C. As shown in FIG. 8, the tentative curve form detecting section 50 is configured to carry out the curve interpolation between the tentative positions $P_{0,i}$ of the respective sensor units $S_i$ in the tentative linear form 71 indicated by a dotted line in FIG. 8. As a result, each tentative arc $L_{0,j}$ is formed, and the tentative curve form 75 indicated by a solid line in FIG. 8 is detected.

The tentative curve form detecting section 50 includes a unit tangent vector calculating section 51 configured to calculate a unit tangent vector at a tentative position $P_{0,i}$ of each sensor unit $S_i$, a rate-of-change calculating section 52 configured to calculate a rate of change of the unit tangent vector between the tentative positions $P_{0,i}$ of the respective sensor units $S_i$ based on the unit tangent vector calculated by the unit tangent vector calculating section 51, and a tentative arc forming section 53 configured to form the tentative arc $L_{0,j}$ between the tentative positions $P_{0,i}$ of the respective sensor units $S_i$ based on the unit tangent vector calculated by the unit tangent vector calculating section 51 and the rate of change calculated by the rate-of-change calculating section 52. When the curve interpolation is performed between the tentative positions $P_{0,i}$ of all the sensor units $S_i$ and then all the tentative arcs $L_{0,j}$ are formed, the tentative curve form 75 is detected.

Here, description will now be given as to a method of using the tentative curve form detecting section 50 to effect the curve interpolation between the tentative positions $P_{0,i}$ of the respective sensor units $S_i$ detected by the sensor tentative position detecting section 40, and thereby detecting the tentative curve form 75. As shown in FIG. 4, the tentative curve form detecting section 50 is configured to carry out the curve interpolation between the tentative positions $P_{0,i}$ of the respective sensor units $S_i$ detected at the step S104 by using the tentative curve $L_{0,j}$, thereby detecting the tentative curve form 75 (a step S105). As described above, if the inter-sensor dimension l is smaller than approximately 50 mm, an error when detecting a form of the inserting section 11 is reduced even though a form between the respective sensor units $S_i$ is assumed to be a linear tentative link $T_{0,j}$ whose dimension is equal to the inter-sensor dimension l. However, a form of the inserting section 11 of the endoscope 10 when inserted into a body cavity is a curve form. Therefore, performing the curve interpolation between the tentative positions $P_{0,i}$ of the respective sensor units $S_i$ is important. Here, although there are differences among products, the inserting section 11 of the endoscope 10 has appropriate elasticity. Therefore, a curvature of the curved form of the inserting section 11 varies only slightly. Therefore, when the curve interpolation is performed on the assumption that a form between the sensor units $S_i$ is the tentative arc $L_{0,j}$ having a radius $R_{0,j}$ (curvature/$R_{0,j}$), it is possible to form the tentative curve form 75 having a small error from an actual curve form of the inserting section 11.

When detecting the tentative curve form 75, the tentative curve form detecting section 50 is configured to sequentially carry out the curve interpolation in accordance with each portion between the tentative positions $P_{0,i}$ of the respective sensor units $S_i$ to form the tentative curve $L_{0,j}$. Here, description will be given as to a method of performing the curve interpolation between the tentative positions $P_{0,j}$ of the respective sensor units $S_i$. Here, the curve interpolation between a kth sensor unit $S_{k-1}$ from the proximal end side and a (k+1)th sensor unit $S_k$ from the proximal end side will be explained. That is, a space between the tentative position $P_{0,k-1}$ and the tentative position $P_{0,k}$ is an interpolation target space between tentative positions as an interpolation target.

Figure 9:
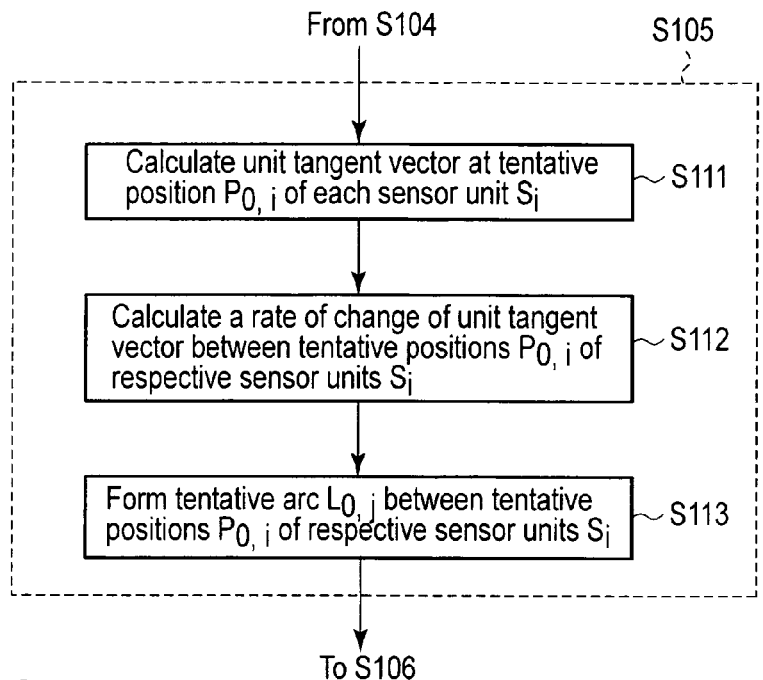
FIG. 9 is a flowchart showing a method of detecting the tentative curve form by the tentative curve form detecting section according to the first embodiment.
Figure 10:
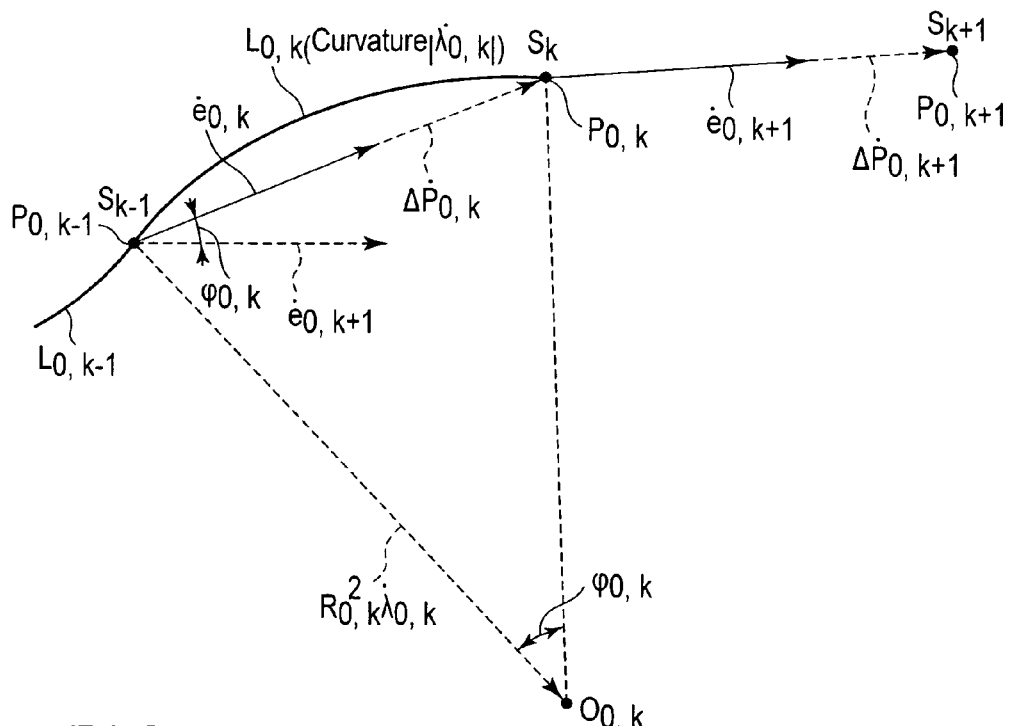
FIG. 10 is a schematic view explaining processing in the tentative curve form detecting section according to the first embodiment.

FIG. 9 is a flowchart showing a method of using the tentative curve form detecting section 50 to detect the tentative curve form 75. FIG. 10 is a view explaining processing in the tentative curve form detecting section 50. As shown in FIG. 9 and FIG. 10, when using the tentative curve form detecting section 50 to perform curve interpolation with respect to a portion between sensors as an interpolation target, which is a portion between the tentative position $P_{0,k-1}$ of the sensor unit $S_{k-1}$ and the tentative position $P_{0,k}$ of the sensor unit $S_k$, the unit tangent vector calculating section 51 is configured to first calculate a unit tangent vector at the tentative position $P_{0,k-1}$ of the sensor unit $S_{k-1}$ and a unit tangent vector at the tentative position $P_{0,k}$ of the sensor unit $S_k$ (a step S111). The unit tangent vector at the tentative position $P_{0,k-1}$ of the sensor unit $S_{k-1}$ is represented as follows:

$$\Delta \dot{P}_{0,k} = \dot{P}_{0,k} - \dot{P}_{0,k-1} \tag{17.1}$$

$$\Delta L_{0,k} = |\Delta \dot{P}_{0,k}| \tag{17.2}$$

$$\dot{e}_{0,k} = \frac{d\dot{P}}{dL}\bigg|_{0,k} = \frac{\Delta \dot{P}_{0,k}}{\Delta L_{0,k}} \tag{17.3}$$

That is, the unit tangent vector at the tentative position $P_{0,k-1}$ is a unit vector of a vector from the tentative position $P_{0,k-1}$ to the tentative position $P_{0,k}$. The unit tangent vector of the sensor unit $S_k$ at the tentative position $P_{0,k}$ can be calculated by using expressions obtained by substituting k in Expression (17.1), Expression (17.2), and Expression (17.3) by k+1. That is, the unit tangent vector at the tentative position $P_{0,k}$ is a unit vector of a vector from the tentative position $P_{0,k}$ to the tentative position $P_{0,k+1}$.

Further, the rate-of-change calculating section 52 is configured to calculate a rate of change of the unit tangent vector between the tentative position $P_{0,k-1}$ of the sensor unit $S_{k-1}$ and the tentative position $P_{0,k}$ of the sensor unit $S_k$ based on the unit tangent vector calculated by the unit tangent calculating section 51 (a step S112). First, a rate-of-change vector of the unit tangent vector between the tentative position $P_{0,k-1}$ and the tentative position $P_{0,k}$ is obtained based on the following expressions:

$$\lambda_{0,k} = \frac{d^2 \dot{P}}{dL^2}\bigg|_{0,k} = \frac{d\dot{e}}{dL}\bigg|_{0,k} = \frac{\dot{e}_{0,k+1} - \dot{e}_{0,k}}{\Delta \bar{L}_{0,k}} \tag{18.1}$$

$$\Delta \bar{L}_{0,k} = \frac{\Delta L_{0,k+1} - \Delta L_{0,k}}{2} \tag{18.2}$$

Furthermore, a magnitude of the rate-of-change vector obtained based on Expression (18.1) and Expression (18.2) is the rate of change of the unit tangent vector between the tentative position $P_{0,k-1}$ and the tentative position $P_{0,k}$.

Moreover, the tentative arc forming section 53 is configured to form the tentative arc $L_{0,k}$ between the tentative position $P_{0,k-1}$ of the sensor unit $S_{k-1}$ and the tentative position $P_{0,k}$ of the sensor unit $S_k$ based on the unit tangent vector calculated by the unit tangent vector calculating section 51 and the rate of change calculated by the rate-of-change calculating section 52 (a step S113). Here, the rate of change of the unit tangent vector between the tentative position $P_{0,k-1}$ and the tentative position $P_{0,k}$ calculated at the step S112 is curvature $1/R_{0,k}$ of the tentative arc $L_{0,k}$. Since a radius $R_{0,k}$ of the tentative arc $L_{0,k}$ is an inverse number of the curvature $1/R_{0,k}$, the radius $R_{0,k}$ of the tentative arc $L_{0,k}$ is as follows:

$$R_{0,k} = \frac{1}{|\lambda_{0,k}|} \tag{19}$$

Moreover, a position of the center $O_{0,k}$ of the tentative arc $L_{0,k}$ in the global coordinate C can be obtained based on the following expression:

$$O_{0,k} = \dot{P}_{0,k-1} + R_{0,k}{}^2 \lambda_{0,k} \tag{20}$$

Additionally, a central angle $\phi_{0,k}$ of the tentative arc $L_{0,k}$ can be obtained by using the unit tangent vector at the tentative position $P_{0,k-1}$ and the unit tangent vector at the tentative position $P_{0,k}$ based on the following expression:

$$\phi_{0,k} = \cos^{-1} \frac{\Delta \dot{P}_{0,k} \cdot \Delta \dot{P}_{0,k+1}}{|\Delta \dot{P}_{0,k}||\Delta \dot{P}_{0,k+1}|} = \cos^{-1}(\dot{e}_{0,k} \cdot \dot{e}_{0,k+1}) \tag{21}$$

Using these parameters enables forming the tentative arc $L_{0,k}$ between the tentative position $P_{0,k-1}$ and the tentative position $P_{0,k}$.

It is to be noted that each tentative arc $L_{0,j}$ other than the tentative arc $L_{0,k}$ can be likewise formed by performing the curve interpolation between a tentative position $P_{0,j-1}$ and a tentative position $P_{0,j}$. That is, when forming the tentative arc $L_{0,j}$, the unit tangent vector calculating section 51 is configured to first calculate a unit tangent vector at the tentative position $P_{0,j-1}$ of the sensor unit $S_{j-1}$ placed on the proximal end side (the side close to the origin in the global coordinate system C) in the interpolation target space between the tentative positions and a unit tangent vector at the tentative position $P_{0,j}$ of the sensor unit $S_j$ placed on the distal end side (the side far from the origin of the global coordinate system C) the interpolation target space between the tentative positions. The unit tangent vector at the tentative position $P_{0,j-1}$ of the sensor unit $S_{j-1}$ can be calculated by using expressions obtained by substituting j for k in Expression (17.1), Expression (17.2), and Expression (17.3), and it is a unit vector of a vector from the tentative position $P_{0,j-1}$ to the tentative position $P_{0,j}$. Further, the unit tangent vector at the tentative position $P_{0,j}$ of the sensor unit $S_j$ can be calculated by using expressions obtained by substituting j+1 for k in Expression (17.1), Expression (17.2), and Expression (17.3), and it is a unit vector of a vector from the tentative position $P_{0,j}$ to the tentative position $P_{0,j+1}$. As a result, a unit tangent vector at the tentative position $P_{0,j}$ of each sensor unit $S_j$ can be calculated (a step S111).

Further, based on the unit tangent vector calculated by the unit tangent vector calculating section 51, the rate-of-change calculating section 52 is configured to calculate a rate of change of the unit tangent vector in the interpolation target space between the tentative positions corresponding to a portion between the tentative position $P_{0,j-1}$ of the sensor unit $S_{j-1}$ and the tentative position $P_{0,j}$ of the sensor unit $S_j$. The rate of change of the unit tangent vector between the tentative position $P_{0,j-1}$ and the tentative position $P_{0,j}$ can be calculated by using expressions obtained by substituting j for k in Expression (18.1) and Expression (18.2). As a result, the rate of change of the unit tangent vector between the tentative positions $P_{0,i}$ of the respective sensor units $S_i$ can be detected (a step S112).

Furthermore, based on the unit tangent vector calculated by the unit tangent vector calculating section 51 and the rate of change calculated by the rate-of-change calculating section 52, the tentative arc forming section 53 is configured to form the tentative arc $L_{0,j}$ in the interpolation target space between the tentative positions, namely, between tentative position $P_{0,j-1}$ of the sensor unit $S_{j-1}$ and the tentative position $P_{0,j}$ of the sensor unit $S_j$. Here, a radium $R_{0,j}$, a center $O_{0,j}$, and a central angle $\phi_{0,j}$ of the tentative arc $L_{0,j}$ can be calculated by using expressions obtained by substituting j for k in Expression (19), Expression (20), and Expression (21). As a result, the tentative arc $L_{0,j}$ between the tentative positions $P_{0,i}$ of the respective sensor units $S_i$ is formed (a step S113). The curve interpolation is carried out between the tentative positions $P_{0,i}$ of all the sensor units $S_i$, and then all the tentative arcs $L_{0,j}$ are formed, thereby detecting the tentative curve form 75.

As shown in FIG. 3, the tentative curve form detecting section 50 is connected to a sensor position correcting section 55 configured to correct a position of each sensor unit $S_i$. The sensor position correcting section 55 is configured to correct a position of each sensor unit $S_i$ based on an absolute value of a difference between an arc length $R_{0,j}\phi_{0,j}$ of each tentative arc $L_{0,j}$ of the tentative curve form 75 detected by the tentative curve form detecting section 50 and the inter-sensor dimension l. Here, the absolute value of the difference between the arc length $R_{0,j}\phi_{0,j}$ of each tentative arc $L_{0,j}$ and the inter-sensor dimension l is assumed to be energy $E_{0,j}$. FIG. 11 is a view showing a position of each sensor unit $S_i$ corrected by the sensor position correcting section 55 from the negative direction toward the positive direction of the Z axis of the global coordinate C. As shown in FIG. 11, the sensor position correcting section 55 is configured to correct each sensor unit $S_i$ from a tentative position $P_{0,i}$ to a final position $P_{F,i}$.

The sensor position correcting section 55 includes a sensor position sequentially compensating section 57 configured to sequentially perform positional compensation from the sensor unit $S_i$ provided on the proximal end side (the side close to the origin of the global coordinate system C). In a state before the sensor position sequentially compensating section 57 performs the positional compensation of each sensor unit $S_i$, each sensor unit $S_i$ has been moved from the tentative position $P_{0,i}$ to a pre-compensation position $Q_{0,i}$ (details will be described later). The sensor position sequentially compensating section 57 is configured to perform the positional compensation with respect to each sensor unit $S_i$ from the pre-compensation position $Q_{0,i}$ to the final position $P_{F,i}$. Moreover, the sensor position correction section 55 includes an uncompensated sensor group moving section 59 configured to parallel translate an uncompensated sensor group 77, that includes the sensor units Si which have not been subjected to the positional compensation, every time the sensor position sequentially compensating section 57 performs the positional compensation of one sensor unit $S_i$. The sensor position sequentially compensating section 57 is configured to perform the positional compensation from the pre-compensation position $Q_{0,i}$ to the final position $P_{F,i}$ of each of all the sensor units $S_i$. Here, the pre-compensation position $Q_{0,i}$ is a position of each sensor unit $S_i$ immediately before performing the positional compensation by the sensor position sequentially compensating section 57. The uncompensated sensor group moving section 59 is configured to parallel translate the uncompensated sensor group 77 a distance corresponding to a compensation amount from the pre-compensation position $Q_{0,i}$ to the final position $P_{F,i}$ of an immediately preceding compensation target sensor 79 which is the sensor unit $S_i$ as a compensation target in immediately preceding positional compensation effected by the sensor position sequentially compensating section 57. As a result, the uncompensated sensor group 77 is parallel translated from a pre-parallel-translation position $U_{a-1,i}$ (a=1, 2, . . . ) to a post-parallel-translation position $U_{a,i}$. Here, a represents the number of times that each sensor unit $S_i$ is parallel translated by the uncompensated sensor group moving section 59. A pre-parallel-translation position $U_{0,i}$ of the first parallel translation of each sensor unit $S_i$ performed by the uncompensated sensor group moving section 59 coincides with the tentative position $P_{0,i}$. Each sensor unit $S_i$ is parallel translated for (i−1) times by the uncompensated sensor group moving section 59. A post-parallel-translation position $U_{i-1,i}$ of each sensor unit $S_i$ in (i−1)th parallel translation carried out by the uncompensated sensor group moving section 59 coincides with the pre-compensation position $Q_{0,i}$. As described above, a position of each sensor unit $S_i$ is corrected from the tentative position $P_{0,i}$ to the final position $P_{F,i}$ based on the positional compensation by the sensor position sequentially compensating section 57 and the parallel translation by the uncompensated sensor group moving section 59.

The sensor position sequentially compensating section 57 includes a sensor moving section 61 configured to move a compensation target sensor 81, which is a positional compensation target, from the pre-compensation position $Q_{0,i}$ more than once. Based on the movement performed by the sensor moving section 61 once, the compensation target sensor 81 moves from a pre-movement position $Q_{t-1,i}$ (t=1, 2, . . . ) to a post-movement position $Q_{t,i}$. Here, t represents the number of times that each sensor unit $S_i$ is moved by the sensor moving section 61. Further, the sensor position sequentially compensating section 57 includes a post-movement arc forming section 62 configured to perform curve interpolation between a final position $P_{F,i}$ of a close-side adjacent sensor 82, that is a sensor unit Si provided to be adjacent to the proximal end side (the side close to the origin of the global coordinate system C) with respect to the compensation target sensor 81, and a post-movement position $Q_{t,i}$ of the compensation target sensor 81. When the curve interpolation is performed between the final position $P_{F,i}$ of the close-side adjacent sensor 82 and the post-movement position $Q_{t,i}$ of the compensation target sensor 81 by the post-movement arc forming section 62, a post-movement arc $L_{t,j}$ is formed.

The sensor position sequentially compensating section 57 includes a movement controlling section 63 configured to control the sensor moving section 61 to repeatedly move the compensation target sensor 81 from the pre-movement position $Q_{t-1,i}$ to the post-movement position $Q_{t,i}$ until an absolute value of a difference between an arc length $R_{t,j}\phi_{t,j}$ of a post-movement arc $L_{t,j}$ formed by the post-movement arc forming section 62 and the inter-sensor dimension l becomes not greater than a predetermined threshold value. Here, the absolute value of the difference between the arc length $R_{t,j}\phi_{t,j}$ of the post-movement arc $L_{t,j}$ and the inter-sensor dimension l is determined to be energy $E_{t,j}$. Furthermore, the sensor position sequentially compensating section 57 includes a final position deciding section 64 configured to decide a post-movement position $Q_{F,i}$ in the last (e.g., Fth) movement by the sensor moving section 61 as a final position $P_{F,i}$ of the compensation target sensor 81. Detailed processing in the sensor moving section 61, the post-movement arc forming section 62, the movement controlling section 63, and the final position deciding section 64 will be described later.

Description will now be given as to a method of correcting a position of each sensor unit $S_i$ by the sensor position correcting section 55. As shown in FIG. 4, the sensor position correcting section 55 is configured to correct a position of each sensor unit $S_i$ based on an absolute value of a difference between an arc length $R_{0,j}\phi_{0,j}$ of each tentative arc $L_{0,j}$ of the tentative curve form 75 detected by the tentative curve form detecting section 50 and the inter-sensor dimension l (a step S106). That is, the position of each sensor unit $S_i$ is corrected based on energy $E_{0,j}$ obtained by the following expression:

$$E_{0,j} = |R_{0,j}\phi_{0,j} - l| \qquad (22)$$

As a result, each sensor unit $S_i$ is corrected from the tentative position $P_{0,i}$ to the final position $P_{F,i}$.

As described above, the tentative curve form detecting section 50 forms the tentative curve form 75 having a small error from an actual curve form of the inserting section 11. However, the tentative curve form detecting section 50 does not perform the curve interpolation between the respective sensor units $S_i$ while considering the inter-sensor dimension l. Additionally, measurement data of each sensor unit $S_i$ has an error due to noise and other factors. Therefore, it is important to correct a position of each sensor unit $S_i$ based on the absolute value of a difference between the arc length $R_{0,j}\phi_{0,j}$ of each tentative arc $L_{0,j}$ and the inter-sensor dimension l while considering the inter-sensor dimension l.

Figure 12:
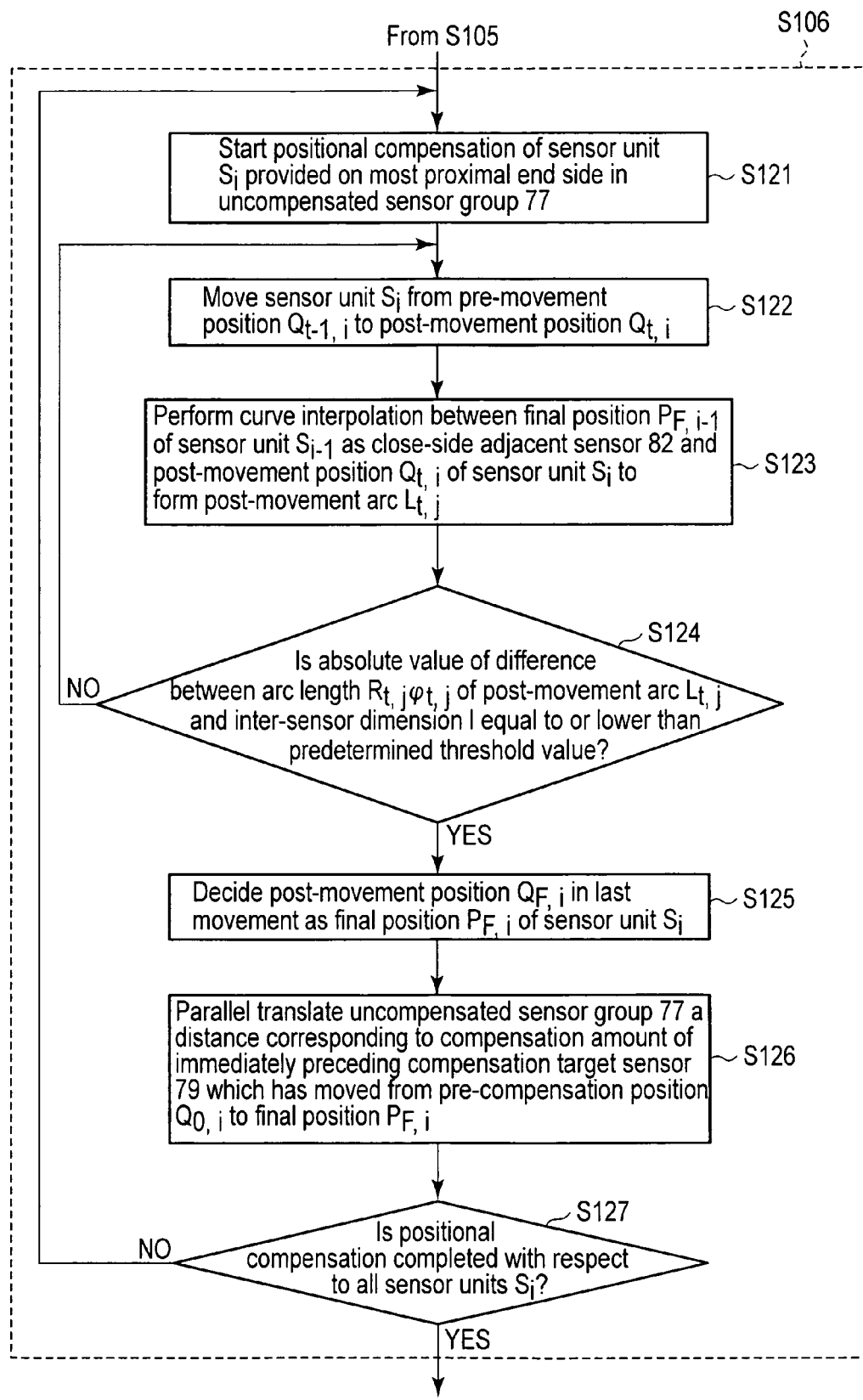
FIG. 12 is a flowchart showing a method of correcting a position of each sensor unit by the sensor position correcting section according to the first embodiment.
Figure 13:
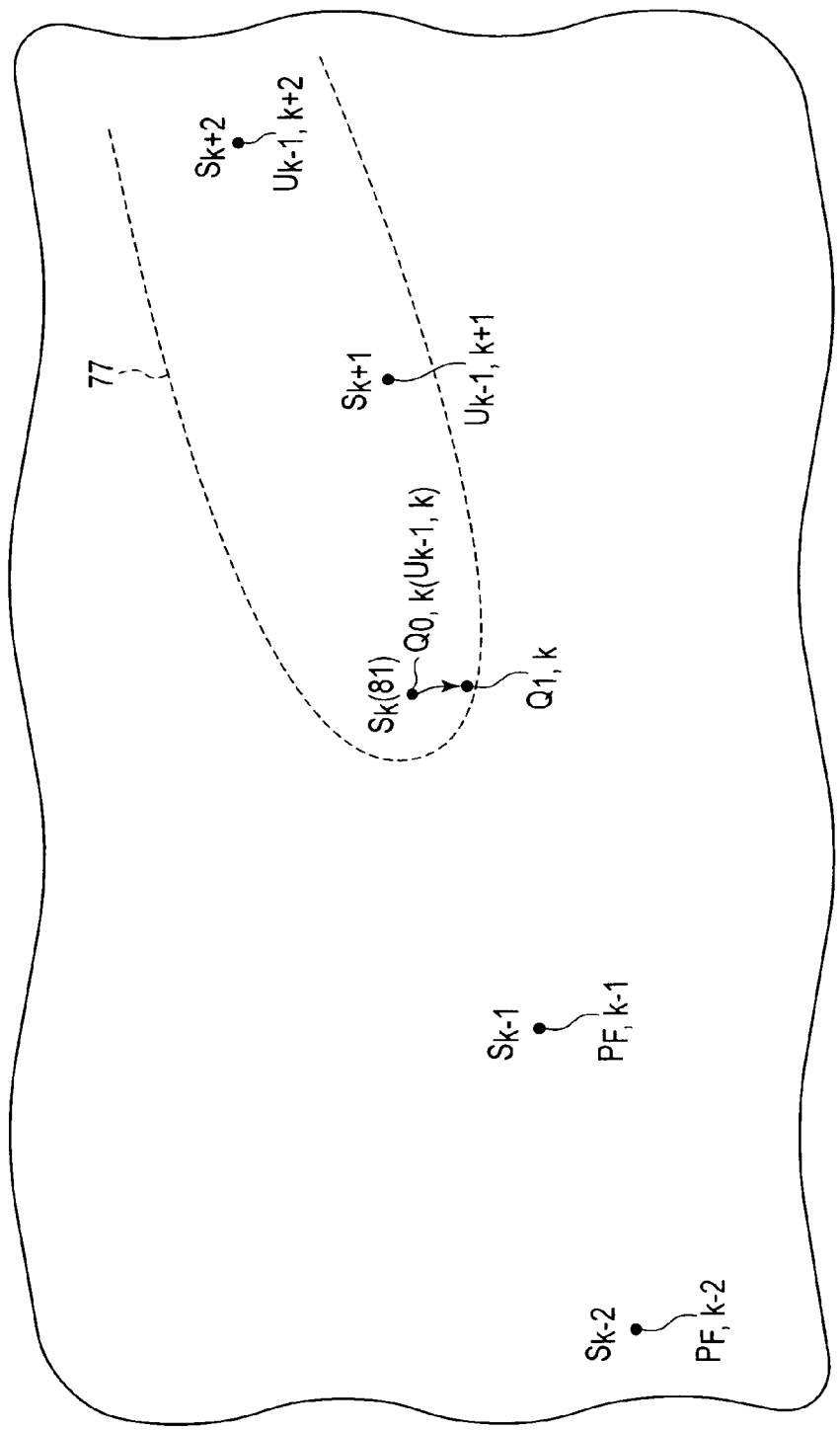
FIG. 13 is a schematic view explaining processing in a sensor position sequentially compensating section of the sensor position correcting section according to the first embodiment.

FIG. 12 is a flowchart showing a method of correcting a position of each sensor unit $S_i$ by the sensor position correcting section 55. FIG. 13 is a view explaining processing carried out by the sensor position sequentially compensating section 57. As shown in FIG. 12, when correcting a position of each sensor unit $S_i$, the sensor position sequentially compensating section 57 is configured to sequentially carry out the positional compensation from the pre-compensation position $Q_{0,i}$ before the positional compensation to the final position $P_{F,i}$ of each of the sensor units $S_i$ starting from the sensor unit $S_i$ provided on the proximal end side (the side close to the origin of the global coordinate system C). Here, the pre-compensation position $Q_{0,i}$ is a position of each sensor unit $S_i$ immediately before the positional compensation is performed by the sensor position sequentially compensating section 57, and it is a position provided when each sensor unit $S_i$ is parallel translated from the tentative position $P_{0,i}$ for (i−1) times by the uncompensated sensor group moving section 59. The sensor position sequentially compensating section 57 is configured to start the positional compensation of the sensor unit $S_i$ provided on the most proximal end side in the uncompensated sensor group 77 (a step S121). That is, as shown in FIG. 13, if the positional compensation from the pre-compensation position $Q_{0,i}$ to the final position $P_{F,i}$ is completed from the first sensor unit to the sensor unit $S_{k-1}$, the sensor position sequentially compensating section 57 is configured to start the positional compensation to the final position $P_{F,k}$ of the sensor unit $S_k$ provided on the most proximal end side in the uncompensated sensor group 77. That is, the sensor unit $S_k$ is the compensation target sensor 81 as a positional compensation target. It is to be noted that the positional compensation of the (k+1)th sensor unit $S_k$ from the proximal end side will be described.

As shown in FIG. 13, when starting the positional compensation of the sensor unit $S_k$ as the compensation target sensor 81, the positional compensation from the pre-compensation position $Q_{0,i}$ to the final position $P_{F,i}$ is completed from the first sensor unit to the sensor unit $S_{k-1}$. At this time, the sensor unit $S_k$ is placed at a pre-compensation position $Q_{0,k}$. In this state, the sensor moving section 61 is configured to move the sensor unit $S_k$ from the position $Q_{0,k}$ to a position $Q_{1,k}$ (a step S122), whereby the sensor unit $S_k$ is moved for the first time.

Figure 14:
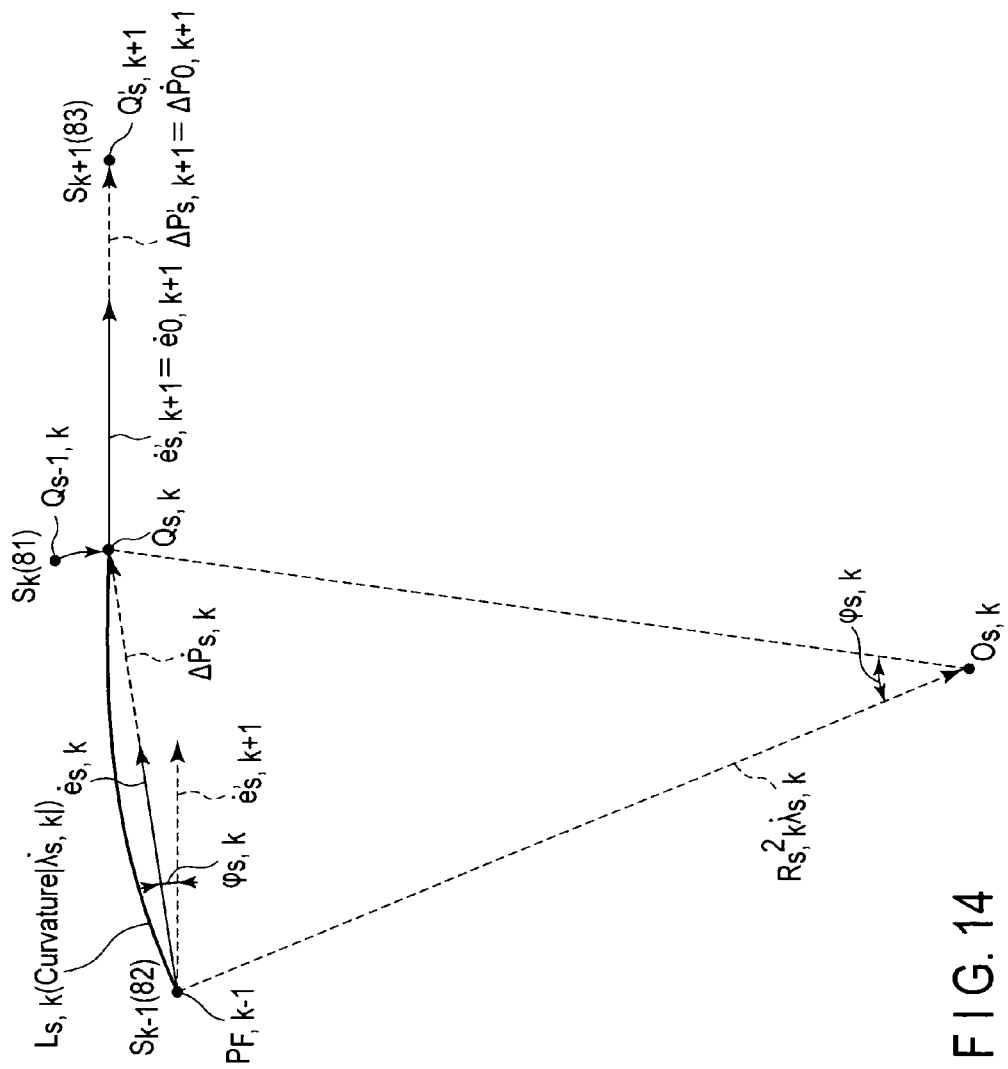
FIG. 14 is a schematic view explaining processing in a sensor moving section and a post-movement arc forming section of the sensor position sequentially compensating section according to the first embodiment.

At this time, the position $Q_{0,k}$ is a pre-movement position, and the position $Q_{1,k}$ is a post-movement position. The sensor moving section 61 is configured to move the sensor unit $S_k$ more than once. FIG. 14 is a view explaining processing in the sensor moving section 61 and the post-movement arc forming section 62. As shown in FIG. 14, in sth movement, the sensor unit $S_k$ as the compensation target sensor 81 moves from a pre-movement position $Q_{s-1,k}$ to a post-movement position $Q_{s,k}$. That is, the sensor unit $S_k$ moves from a pre-movement position $Q_{t-1,k}$ to a post-movement position $Q_{t,k}$ by the movement performed once by the sensor moving section 61 (the step S122).

Further, the post-movement arc forming section 62 is configured to carry out the curve interpolation between a final position $P_{F,k-1}$ of the sensor unit $S_{k-1}$ provided to be adjacent to the proximal end side of the sensor unit $S_k$ and the post-movement position $Q_{t,k}$ of the sensor unit $S_k$ every time the sensor moving section 61 moves the sensor unit $S_k$ once, thereby forming a post-movement arc $L_{t,k}$ (a step S123). As shown in FIG. 14, after sth movement, the curve interpolation is carried out between the final position $P_{F,k-1}$ of the sensor unit $S_{k-1}$ and the post-movement position $Q_{s,k}$ of the sensor unit $S_k$, thereby forming a post-movement arc $L_{s,k}$. Here, the sensor unit $S_{k-1}$ is the close-side adjacent sensor 82 provided to be adjacent to the side close to the origin of the global coordinate system C with respect to the sensor unit $S_k$ which is the compensation target sensor 81.

When forming the post-movement arc $L_{s,k}$ after the sth movement of the sensor unit $S_k$, a unit tangent vector at the final position $P_{F,k-1}$ of the sensor unit $S_{k-1}$ and a unit tangent vector at the post-movement position $Q_{s,k}$ of the sensor unit $S_k$ are calculated. The unit tangent vector at the final position $P_{F,k-1}$ of the sensor unit $S_{k-1}$ is as follows:

$$\Delta \dot{P}_{s,k} = \dot{Q}_{s,k} - \dot{P}_{F,k-1} \qquad (23.1)$$

$$\Delta l_{s,k} = |\Delta \dot{P}_{s,k}| \qquad (23.2)$$

$$\dot{e}_{s,k} = \left.\frac{d\dot{P}}{dL}\right|_{s,k} = \frac{\Delta \dot{P}_{s,k}}{\Delta L_{s,k}} \qquad (23.3)$$

That is, the unit tangent vector at the final position $P_{F,k-1}$ is a unit vector of a vector from the final position $P_{F,k-1}$ to the post-movement position $Q_{s,k}$. Furthermore, when calculating the unit tangent vector at the post-movement position $Q_{s,k}$, a sensor unit $S_{k+1}$ which is a far-side adjacent sensor 83 provided to be adjacent to the side far from the origin of the global coordinate system C with respect to the sensor unit $S_k$, which is the compensation target sensor 81, is assumed to be arranged at a position $Q'_{s,k+1}$. Here, a vector from the post-movement position $Q_{s,k}$ to the position $Q'_{s,k+1}$ has a direction and a magnitude equal to those of a vector from a tentative position $P_{0,k}$ of the sensor unit $S_k$ to a tentative position $P_{0,K+1}$ of the sensor unit $S_k$. A unit vector at the post-movement position $Q_{s,k}$ of the sensor unit $S_{k+1}$ is as follows:

$$\Delta \dot{P}'_{s,k+1} = \dot{Q}'_{s,k+1} - \dot{Q}_{s,k} \qquad (24.1)$$

$$\Delta L'_{s,k+1} = |\Delta \dot{P}'_{s,k+1}| \qquad (24.2)$$

$$\dot{e}'_{s,k+1} = \left.\frac{d\dot{P}'}{dL'}\right|_{s,k+1} = \frac{\Delta \dot{P}'_{s,k+1}}{\Delta L'_{s,k+1}} \qquad (24.3)$$

That is, the unit tangent vector at the post-movement position $Q_{s,k}$ is a unit vector of a vector from the post-movement position $Q_{s,k}$ to the position $Q'_{s,k+1}$ of the sensor unit $S_{k+1}$. Therefore, the unit tangent vector at the post-movement position $Q_{s,k}$ has the same direction as the unit tangent vector obtained by substituting k+1 for k in Expression (17.1) to Expression (17.3).

Moreover, based on the unit tangent vector calculated by using Expression (23.1) to Expression (23.3), Expression (24.1), and Expression (24.3), a rate of change of the unit tangent vector between the final position $P_{F,k-1}$ of the sensor unit $S_{k-1}$ and the post-movement position $Q_{s,k}$ of the sensor unit $S_k$ is calculated. First, a rate-of-change vector of the unit tangent vector between the final position $P_{F,k-1}$ and the post-movement position $Q_{s,k}$ is obtained based on the following expressions:

$$\lambda_{s,k} = \frac{d^2 \dot{P}}{dL^2}\bigg|_{s,k} = \frac{d\dot{e}}{dL}\bigg|_{s,k} = \frac{\dot{e}_{s,k+1} - \dot{e}_{s,k}}{\Delta \overline{L}_{s,k}} \quad (25.1)$$

$$\Delta \overline{L}_{s,k} = \frac{\Delta L'_{s,k+1} - \Delta L_{s,k}}{2} \quad (25.2)$$

Additionally, a magnitude of the rate-of-change vector obtained based on Expression (25.1) and Expression (25.2) serves as a rate of change of the unit tangent vector between the final position $P_{F,k-1}$ and the post-movement position $Q_{s,k}$.

Based on the unit tangent vector calculated by Expression (23.1) to Expression (23.3) and Expression (24.1) to Expression (24.3) and the rate of change calculated by Expression (25.1) and Expression (25.2), a post-movement arc $L_{s,k}$ is formed between the final position $P_{F,k-1}$ of the sensor unit $S_{k-1}$ and the post-movement position $Q_{s,k}$ of the sensor unit $S_k$. Here, the rate of change of the unit tangent vector between the final position $P_{F,k-1}$ and the post-movement position $Q_{s,k}$ calculated by using Expression (25.1) and Expression (25.2) is curvature $1/R_{s,k}$ of the post-movement arc $L_{s,k}$. A radius $R_{s,k}$ of the post-movement arc $L_{s,k}$ is an inverse number of the curvature $1/R_{s,k}$, and hence the radius $R_{s,k}$ of the post-movement arc $L_{s,k}$ is as follows:

$$R_{s,k} = \frac{1}{|\lambda_{s,k}|} \quad (26)$$

Further, a position of a center $O_{s,k}$ of the post-movement arc $L_{s,k}$ can be obtained based on the following expression:

$$O_{s,k} = \dot{P}_{F,k-1} + R_{s,k}{}^2 \ddot{\lambda}_{s,k} \quad (27)$$

Furthermore, a central angle $\phi_{s,k}$ of the post-movement arc Ls, k can be obtained by using the unit tangent vector at the final position $P_{F,k-1}$ and the unit tangent vector at the post-movement position $Q_{s,k}$ based on the following expression:

$$\phi_{s,k} = \cos^{-1} \frac{\Delta \dot{P}_{s,k} \cdot \Delta \dot{P}'_{s,k+1}}{|\Delta \dot{P}_{s,k}||\Delta \dot{P}'_{s,k+1}|} = \cos^{-1}(\dot{e}_{s,k} \cdot \dot{e}'_{s,k}) \quad (28)$$

The post-movement arc $L_{s,k}$ between the final position $P_{F,k-1}$ and the post-movement position $Q_{s,k}$ is formed by using these parameters.

It is to be noted that the processing of forming the post-movement arc $L_{s,k}$ after the sth movement of the sensor unit $S_k$ has been described, and a post-movement arc $L_{t,k}$ between the final position $P_{F,k-1}$ of the sensor unit $S_{k-1}$ and the post-movement position $Q_{t,k}$ of the sensor unit $S_k$ is likewise formed by using expressions obtained by substituting t for s in Expression (23.1) to Expression (28).

Moreover, after the post-movement arc $L_{t,k}$ is formed, an absolute value of a difference between an arc length $R_{t,k}\phi_{t,k}$ of the post-movement arc $L_{t,k}$ and the inter-sensor dimension l is calculated by the movement controlling section 63 (a step S124). Here, the absolute value of the difference between the arc length $R_{t,k}\phi_{t,k}$ of the post-movement arc $L_{t,k}$ and the inter-sensor dimension l is assumed to be energy $E_{t,k}$, and this energy can be provided by the following expression:

$$E_{t,k} = |R_{t,k}\phi_{t,k} - l| \quad (29)$$

When the energy $E_{t,k}$ is larger than a predetermined threshold value (a step S124—No), the processing returns to the step S122, and the sensor moving section 61 is configured to further move the sensor unit $S_k$ from the position $Q_{t,k}$. When the energy $E_{s,k}$ is larger than the threshold value after the sth movement of the sensor unit $S_k$, the sensor moving section 61 is configured to perform (s+1)th movement. Based on the (s+1)th movement, the sensor unit $S_k$ moves from the pre-movement position $Q_{s,k}$ to the post-movement position $Q_{s+1,k}$. As described above, the sensor moving section 61 is controlled by the movement controlling section 63 to repeatedly perform the movement of the sensor unit $S_k$ as the compensation target sensor 81 from the pre-movement position $Q_{t-1,k}$ to the post-movement position $Q_{t,k}$ until the energy $E_{t,k}$ becomes equal to or below the predetermined threshold value.

If the energy $E_{t,k}$ is not greater than the predetermined threshold value (the step S124—Yes), the processing advances to the next step. Further, the final position deciding section 64 is configured to decide the post-movement position $Q_{F,k}$ in the last (e.g., fth) movement of the sensor unit $S_k$ by the sensor moving section 61 as the final position $P_{F,k}$ of the sensor unit $S_k$ (a step S125), which is the compensation target sensor 81. As described above, the positional compensation of the sensor unit $S_k$ from the pre-compensation position $Q_{0,k}$ to the final position $P_{F,k}$ is completed.

It is to be noted that the sensor position sequentially compensating section 57 performs the positional compensation to the final position $P_{t,k}$ with respect to each sensor unit $S_i$ other than the sensor unit $S_k$ like the sensor unit $S_k$. That is, the sensor moving section 61 is configured to move the sensor unit $S_i$ from a pre-movement position $Q_{t-1,i}$ to a post-movement position $Q_{t,i}$ (the step S122). Further, the post-movement arc forming section 62 is configured to perform the curve interpolation between a final position $P_{F,i-1}$ of a sensor unit $S_{i-1}$, which is the close-side adjacent sensor 82 provided to be adjacent to the proximal end side of the sensor unit $S_i$, and the post-movement position Qt, i of the sensor unit $S_i$ every time the sensor moving section 61 moves the sensor unit $S_i$ once, thereby forming a post-movement arc $L_{t,j}$ (the step S123).

Furthermore, after forming the post-movement arc $L_{t,j}$, the movement controlling section 63 is configured to calculate energy $E_{t,j}$ which is an absolute value of a difference between an arc length $R_{t,j}\phi_{t,j}$ of the post-movement arc $L_{t,j}$ and the inter-sensor dimension l (the step S124). If the energy $E_{t,j}$ is larger than a predetermined threshold value (the step S124—No), the processing returns to the step S122, and the sensor moving section 61 is configured to further move the sensor unit $S_i$ from the position $Q_{t,i}$. If the energy $E_{t,j}$ is not greater than the predetermined threshold value (the step S124—Yes), the processing advances to the next step. Moreover, the final position deciding section 64 is configured to decide a post-movement position $Q_{F,i}$ in the final movement of the sensor unit $S_i$ performed by the sensor moving section 61 as a final position $P_{F,i}$ of the sensor unit $S_i$ (the step S125), which is the compensation target sensor 81. As described above, the positional compensation of the sensor unit $S_i$ from the pre-compensation position $Q_{0,i}$ to the final position $P_{F,i}$ is completed.

Figure 15:
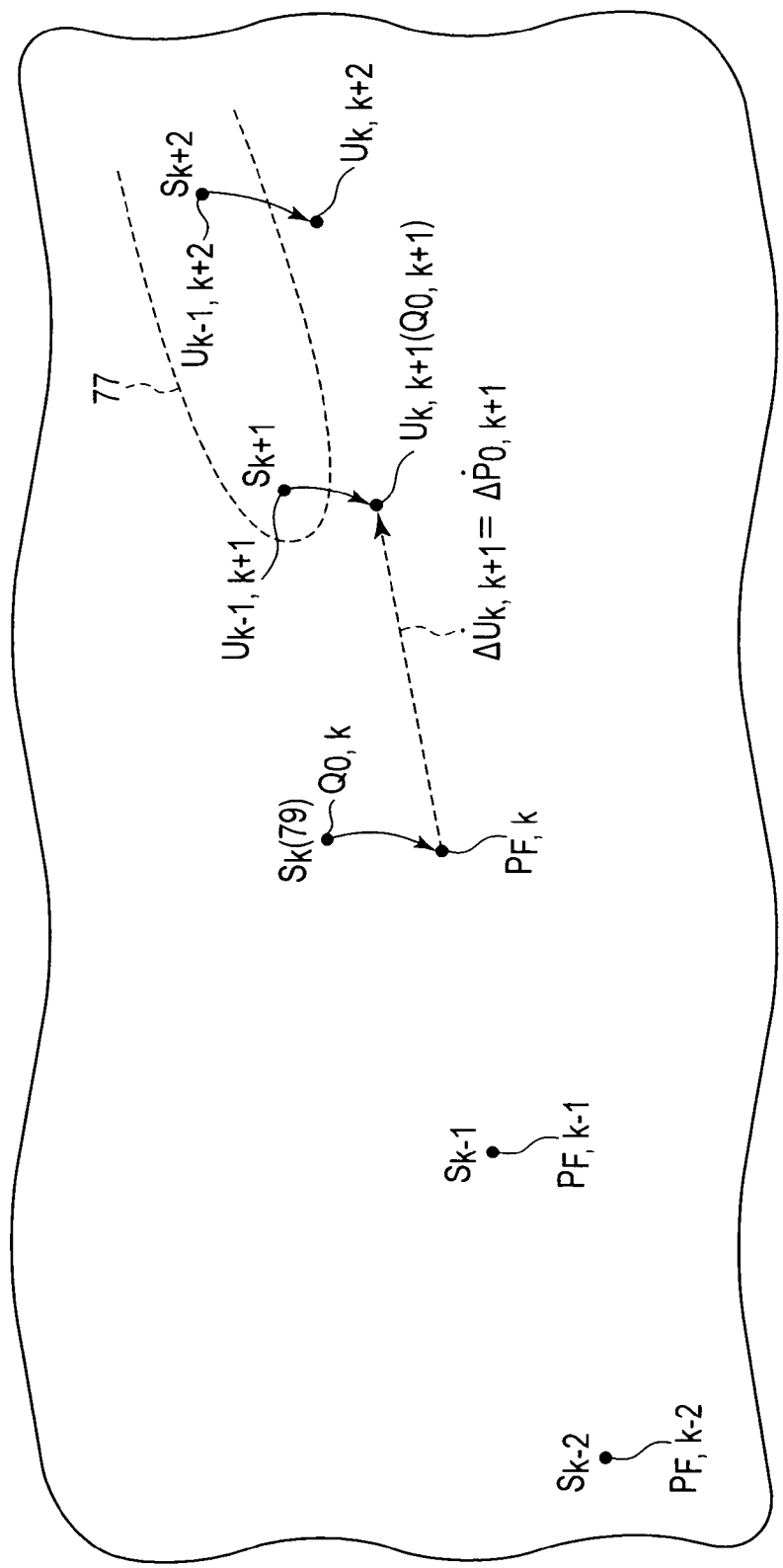
FIG. 15 is a schematic view explaining processing in an uncompensated sensor group moving section of the sensor position correcting section according to the first embodiment.

Additionally, the uncompensated sensor group moving section 59 is configured to parallel translate the uncompensated sensor group 77, that includes sensor units $S_i$ which have not been subjected to the positional compensation, every time the sensor position sequentially compensating section 57 carries out the positional compensation of one sensor unit $S_i$ (a step S126). FIG. 15 is a view explaining processing in the uncompensated sensor group moving section 59. As shown in FIG. 15, in a state that positional compensation from a pre-compensation position $Q_{0,k}$ to a final position $P_{F,k}$ of a sensor unit $S_k$ is completed by the sensor position sequentially compensating section 57, sensor units $S_{k+1}$ to $S_N$ are the uncompensated sensor group 77 which has not been subjected to the positional compensation. Further, the sensor unit $S_k$ is the immediately preceding compensation target sensor 79 as a compensation target in the immediately preceding positional compensation carried out by the sensor position sequentially compensating section 57.

In this state, the uncompensated sensor group moving section 59 is configured to parallel translate the uncompensated sensor group 77 a distance corresponding to a compensation amount from the pre-compensation position $Q_{0,k}$ to the final position $P_{F,k}$ of the sensor unit $S_k$ as the immediately preceding compensation target sensor 79. As a result, each sensor unit $S_i$ in the uncompensated sensor group 77 moves from a pre-parallel-translation position $U_{k-1,i}$ to a post-parallel-translation position $U_{k,i}$. Here, the pre-parallel-translation position $U_{k-1,i}$ of each sensor unit $S_i$ in the uncompensated sensor group 77 is a position provided when each sensor unit $S_i$ is moved from a tentative position $P_{0,i}$ for (k−1) times by the uncompensated sensor group moving section 59, and this parallel translation achieves k times of the parallel translation of each sensor unit $S_i$ in the uncompensated sensor group 77 by the uncompensated sensor group moving section 59. Furthermore, a post-parallel-translation position $U_{k,k+1}$ of the sensor unit $S_{k+1}$ coincides with the pre-compensation position $Q_{0,k+1}$, and a vector from the final position $P_{F,k}$ of the sensor unit $S_k$ to the post-parallel-translation position $U_{k,k+1}$ of the sensor unit $S_{k+1}$ has a direction and a magnitude equal to those of a vector from the tentative position $P_{0,k}$ of the sensor unit $S_k$ to the tentative position $P_{0,k+1}$ of the sensor unit $S_{k+1}$.

It is to be noted that the uncompensated sensor group 77 is parallel translated even in a state that the positional compensation of each sensor unit $S_i$ other than the sensor unit $S_k$ to the final position PF, i is completed, like the sensor unit $S_k$. That is, the uncompensated sensor group moving section 59 is configured to translate the uncompensated sensor group 77 a distance corresponding to a compensation amount of the immediately preceding target sensor 79 from the pre-compensation position $Q_{0,i}$ to the final position $P_{F,i}$ performed by the sensor position sequentially compensating section 57 (a step S126). As a result, the uncompensated sensor group 77 is parallel translated from a pre-parallel-translation position $U_{a-1,i}$ to a post-parallel-translation position $U_{a,i}$.

Furthermore, as shown in FIG. 12, whether the positional compensation is completed with respect to all the sensor units $S_i$ is confirmed (a step S127). When the positional compensation is completed with respect to all the sensor units $S_i$ (the step S127—Yes), the processing advances to the next step. When the positional compensation is not completed with respect to all the sensor units $S_i$ (the step S127—No), the processing returns to the step S121, and the sensor position sequentially compensating section 57 carries out the positional compensation of the sensor unit $S_i$ on the most proximal end side in the uncompensated sensor group 77. That is, the steps S121 to S126 are repeatedly performed until the positional compensation is completed with respect to all the sensor units $S_i$. As described above, based on the positional compensation from the pre-compensation position $Q_{0,i}$ to the final position $P_{F,i}$ performed by the sensor position sequentially compensating section 57 and the parallel translation effected by the uncompensated sensor group moving section 59, a position of each sensor unit $S_i$ is corrected from the tentative position $P_{0,i}$ to the final position $P_{F,i}$.

Figure 16:
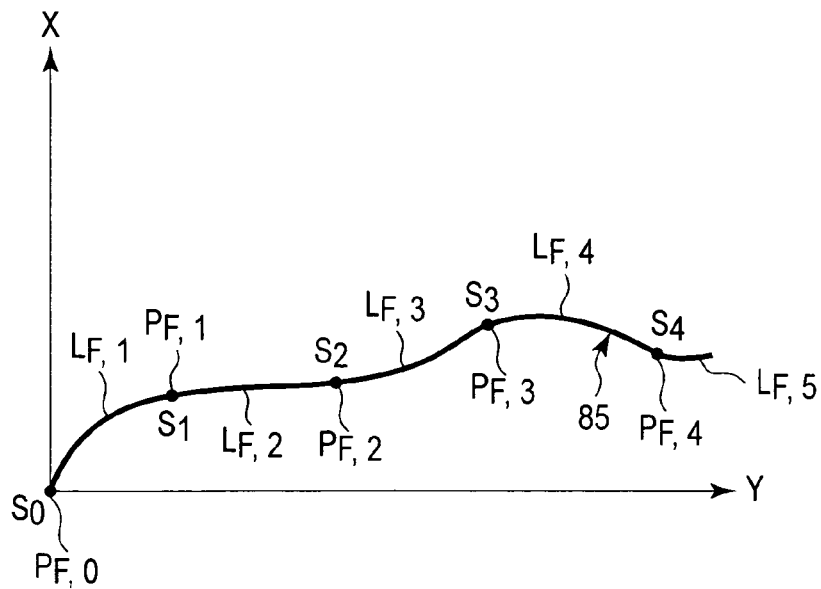
FIG. 16 is a schematic view showing a final curve form of the inserting section of the endoscope detected by the final curve form detecting section of the endoscopic form detection device according to the first embodiment.

As shown in FIG. 3, the sensor position correcting section 55 is connected to a final curve form detecting section 65. The final curve form detecting section 65 is configured to carry out the curve interpolation between final positions $P_{F,i}$ of respective sensor units $S_i$ by using a final arc $L_{F,j}$, thereby detecting a final curve form 85 of the inserting section 11. FIG. 16 is a view showing the final curve form 85 of the inserting section 11 of the endoscope 10 detected by the final curve form detecting section 65 from the negative direction toward the positive direction of the Z axis of the global coordinate C. As shown in FIG. 16, the final curve form detecting section 65 is configured to perform the curve interpolation between the final positions $P_{F,i}$ of the respective sensor units $S_i$. As a result, each final arc $L_{F,j}$ is formed, and the final curve form 85 is detected.

The final curve form detecting section 65 includes a parameter calculating section 67 configured to calculate a parameter of each final arc $L_{F,j}$ based on the final position $P_{F,i}$ of each sensor unit $S_i$, and a final arc forming section 69 configured to form the final arc $P_{F,i}$ based on the parameter calculated by the parameter calculating section 67. The final arc forming section 69 is configured to carry out the curve interpolation between the final positions $P_{F,i}$ of the respective sensor units $S_i$ at a constant angular velocity with respect to a change in parametric variable t based on an interpolation function $L_{F,j}(t)$ using a quaternion and the parametric variable t, thereby forming the final arc $L_{F,j}$.

A drawing section 45 is connected to the final curve form detecting section 65. The final curve form 85 of the inserting section 11 in the global coordinate system C detected by the final curve form detecting section 65 is drawn by the drawing section 45. An operator can confirm the final curve form 85 drawn by the drawing section 45 in a display section 47.

Here, description will now be given as to a method of performing the curve interpolation between the final positions $P_{F,i}$ of the respective sensor units $S_i$ subjected to the positional correction by the sensor position correcting section 55 to detect the final curve form 85. As shown in FIG. 4, the final curve form detecting section 65 configured to perform the curve interpolation between the final positions $P_{F,i}$ of the respective sensor units $S_i$ which have been subjected to the positional correction at the step S106 by using the final arc $L_{F,j}$, thereby detecting the final curve form 85 (a step S107). As a result, the curve interpolation is effected between the final positions $P_{F,i}$ of the respective sensor units $S_i$ while considering the inter-sensor dimension l, whereby the finial curve form 85 is detected with a high detection accuracy.

When detecting the final curve form 85, the final curve form detecting section 65 is configured to sequentially carry out the curve interpolation between the final positions $P_{F,i}$ of the respective sensor units $S_i$ to form the final arc $L_{F,j}$. Here, description will now be given as to a method of performing the curve interpolation between the final positions $P_{F,i}$ of the respective sensor units $S_i$ by using the final curve form detecting section 65. Here, the curve interpolation between a kth sensor unit $S_{k-1}$ from the proximal end side and a (k+1)th sensor unit $S_k$ from the proximal end side will be explained. That is, a portion between the final position $P_{F, k-1}$ and the final position $P_{F, k}$ is an interpolation target space between final positions as an interpolation target.

Figure 17:
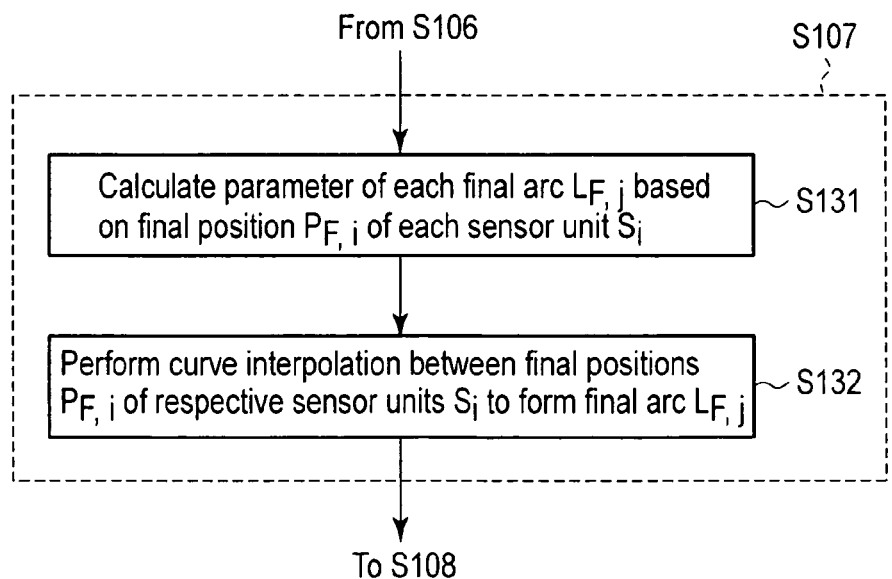
FIG. 17 is a flowchart showing a method of detecting the final curve form by the final curve form detecting section according to the first embodiment.
Figure 18:
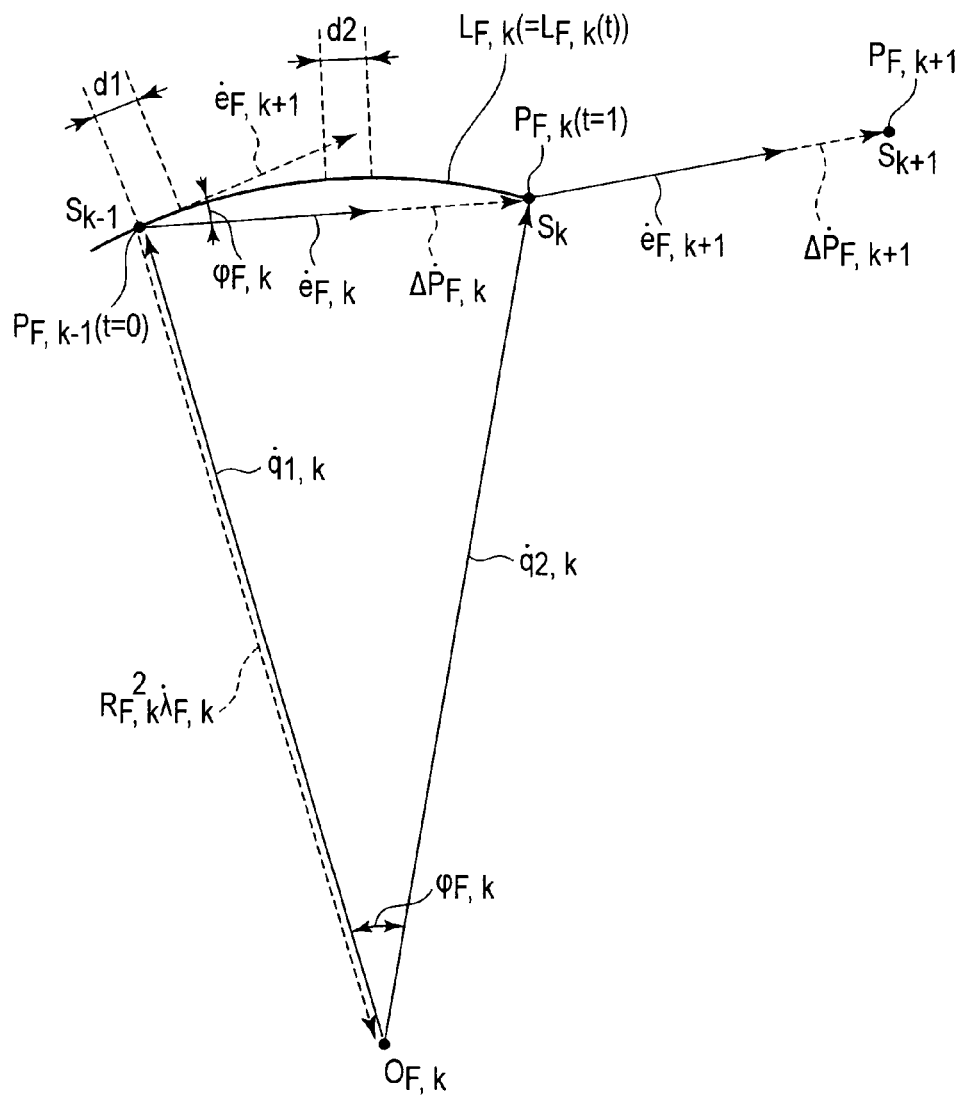
FIG. 18 is a schematic view explaining processing in the final curve form detecting section according to the first embodiment.

FIG. 17 is a flowchart showing a method of detecting the final curve form 85 by the final curve form detecting section 65. FIG. 18 is a view explaining processing in the final curve form detecting section 65. As shown in FIG. 17 and FIG. 18, when performing the curve interpolation with respect to the space between the final positions as an interpolation target, which is a portion between a final position $P_{F, k-1}$ of a sensor unit $S_{k-1}$ and a final position $P_{F, k}$ of a sensor unit $S_k$, by the final curve form detecting section 65, the parameter calculating section 67 is configured to first calculate a parameter of a final arc $L_{F, k}$ based on the final position $P_{F, k-1}$ and the final position $P_{F, k}$ (a step S131).

At this time, a unit tangent vector at the final position $P_{F, k-1}$ of the sensor unit $S_{k-1}$ and a unit tangent vector at the final position $P_{F, k}$ of the sensor unit $S_k$ are calculated. The unit tangent vector at the final position $P_{F, k-1}$ of the sensor unit $S_{k-1}$ is as follows:

$$\Delta \dot{P}_{F,k} = \dot{P}_{F,k} - \dot{P}_{F,k-1} \tag{30.1}$$

$$\Delta L_{F,k} = |\Delta \dot{P}_{F,k}| \tag{30.2}$$

$$\dot{e}_{F,k} = \left.\frac{d\dot{P}}{dL}\right|_{F,k} = \frac{\Delta \dot{P}_{F,k}}{\Delta L_{F,k}} \tag{30.3}$$

That is, the unit tangent vector at the final position $P_{F, k-1}$ is a unit vector of a vector from the final position $P_{F, k-1}$ to the final position $P_{F, k}$. The unit tangent vector at the final position $P_{F, k}$ of the sensor unit $S_k$ can be calculated by using expressions obtained by substituting k+1 for k in Expression (30.1), Expression (30.2), and Expression (30.3). That is, the unit tangent vector at the final position $P_{F, k}$ is a unit vector of a vector from the final position $P_{F, k}$ to the final position $P_{F, k+1}$.

Additionally, based on the unit tangent vectors at the final positions $P_{F, k-1}$ and $P_{F, k}$, a rate of change in unit tangent vector between the final position $P_{F, k-1}$ of the sensor unit $S_{k-1}$ and the final position $P_{F, k}$ of the sensor unit $S_k$ is calculated. First, a rate-of-change vector of a unit tangent vector between the final position $P_{F, k-1}$ and the final position $P_{F, k}$ is obtained based on the following expressions:

$$\lambda_{F,k} = \left.\frac{d^2\dot{P}}{dL^2}\right|_{F,k} = \left.\frac{d\dot{e}}{dL}\right|_{F,k} = \frac{\dot{e}_{F,k+1} - \dot{e}_{F,k}}{\Delta \bar{L}_{F,k}} \tag{31.1}$$

$$\Delta \bar{L}_{F,k} = \frac{\Delta L_{F,k+1} - \Delta L_{F,k}}{2} \tag{31.2}$$

Further, a magnitude of the rate-of-change vector obtained by Expression (31.1) and Expression (31.2) is a rate of change of the unit tangent vector between the final position $P_{F, k-1}$ and the final position $P_{F, k}$.

Furthermore, based on the unit tangent vector and the rate of change calculated by Expression (30.1) to Expression (31.2), a parameter of the final arc $L_{F, k}$ between the final position $P_{F, k-1}$ of the sensor unit $S_{k-1}$ and the final position $P_{F, k}$ of the sensor unit $S_k$ is calculated. Here, since a radius $R_{F, k}$ of the final arc $L_{F, k}$ is an inverse number of a rate of change calculated by using Expression (31.1) and Expression (31.2), the following expression can be achieved:

$$R_{F,k} = \frac{1}{|\lambda_{F,k}|} \tag{32}$$

Moreover, since a position of a center $O_{F, k}$ of the final arc $L_{F, k}$ in the global coordinate C can be calculated by the following expression:

$$O_{F,k} = \dot{P}_{F,k-1} + R_{F,k}^2 \lambda_{F,k} \tag{33}$$

Additionally, a central angle $\phi_{F, k}$ of the final arc $L_{F, k}$ can be calculated based on the following expression:

$$\phi_{F,k} = \cos^{-1}\frac{\Delta \dot{P}_{F,k} \cdot \Delta \dot{P}_{F,k+1}}{|\Delta \dot{P}_{F,k}||\Delta \dot{P}_{F,k+1}|} = \cos^{-1}(\dot{e}_{F,k} \cdot \dot{e}_{F,k+1}) \tag{34}$$

It is to be noted that the parameter calculating section 67 can also calculate a parameter of each final arc $L_{F, j}$ other than the final arc $L_{F, k}$ by using expressions obtained by substituting j for k in Expression (30.1) to Expression (34), like the final arc $L_{F, k}$. That is, based on the final position $P_{F, i}$ of each sensor unit $S_i$, a parameter of each final arc $L_{F, j}$ is calculated (a step S131).

Further, based on the parameter of the final arc $L_{F, j}$ calculated by the parameter calculating section 67, the final arc forming section 69 is configured to carry out the curve interpolation between the final positions $P_{F, i}$ of the respective sensor units $S_i$ to form each final arc $L_{F, j}$ (a step S132). The final arc $L_{F, j}$ is formed based on an interpolation function using a quaternion and a parametric variable.

Here, the quaternion is a number obtained by expanding a complex number, and it can be represented by the following expression:

$$q = w + xi + yj + zk \tag{35}$$

Each of i, j, and k in Expression (35) represents an imaginary unit and meets the following relationships:

$$i^2 = j^2 = k^2 = -1 \tag{36.1}$$

$$ij = k \tag{36.2}$$

$$ji = -k \tag{36.3}$$

$$jk = i \tag{36.4}$$

$$kj = -i \tag{36.5}$$

$$ki = j \tag{36.6}$$

$$ik = -j \tag{36.7}$$

As shown in FIG. 18, when forming the final arc $L_{F, k}$ between the final position $P_{F, k-1}$ of the sensor unit $S_{k-1}$ and the final position $P_{F, k}$ of the sensor unit $S_k$, in the global coordinate system C, a vector from the center $O_{F, k}$ of the final arc $L_{F, k}$ to the final position $P_{F, k-1}$ of the sensor unit $S_{k-1}$ is calculated. The vector from the center $O_{F, k}$ to the final position $P_{F, k-1}$ is as follows:

$$\dot{q}_{1,k} = (x_{1,k}, y_{1,k}, z_{1,k}) \tag{37}$$

Further, in the global coordinate system C, a vector from the center $O_{F, k}$ of the final arc $L_{F, k}$ to the final position $P_{F, k}$ of the sensor unit $S_k$ is calculated. The vector from the center $O_{F, k}$ to the final position $P_{F, k}$ is as follows:

$$\dot{q}_{2,k} = (x_{2,k}, y_{2,k}, z_{2,k}) \tag{38}$$

The vector calculated by Expression (37) is represented by a quaternion as follows:

$$q_{1,k} = x_{1,k} i + y_{1,k} j + z_{1,k} k \quad (39)$$

Likewise, the vector calculated by Expression (38) is represented by a quaternion as follows:

$$q_{2,k} = x_{2,k} i + y_{2,k} j + z_{2,k} k \quad (40)$$

That is, an X axis directions component of the calculated vector in the global coordinate system C is a component of an imaginary number i of the quaternion. Likewise, a Y axis directions component of the vector in the global coordinate system C is a component of an imaginary number j of the quaternion, and a Z axis directions component of the vector in the global coordinate system C is a component of an imaginary number k of the quaternion.

Furthermore, the quaternions in Expression (39) and Expression (40) are used to define the following function $L'_{F,k}(t)$. The function $L'_{F,k}(t)$ is represented as follows:

$$L'_{F,k}(t) = q_{1,k} \sin(1-t)\phi_{F,k} + q_{2,k} \sin t\phi_{F,k} \quad (41)$$

where t is a parametric variable. For normalization, when both sides of Expression (41) are divided by $\sin \phi_{F,k}$, the following expression can be obtained, and an interpolation function $L_{F,k}(t)$ is calculated:

$$L_{F,k}(t) = q_{1,k} \frac{\sin(1-t)\phi_{F,k}}{\sin\phi_{F,k}} + q_{2,k} \frac{\sin t\phi_{F,k}}{\sin\phi_{F,k}} \quad (0 \le t \le 1) \quad (42)$$

Moreover, when t is changed from 0 to 1 using the interpolation function $L_{F,k}(t)$, the curve interpolation is effected between the final position $P_{F,k-1}$ of the sensor unit $S_{k-1}$ and the final position $P_{F,k}$ of the sensor unit $S_k$ to form the final arc $L_{F,k}$. At this time, the curve interpolation is performed between the final position $P_{F,k-1}$ and the final position $P_{F,k}$ at a constant angular velocity with respect to a change in the parametric variable t. For example, a distance d1 interpolated during a change of t from 0 to 0.1 is equal to a distance d2 interpolated during a change of t from 0.5 to 0.6 (see FIG. 18). Therefore, since a change in angular velocity does not have to be considered while interpolating a portion (space) between the final position $P_{F,k-1}$ and the final position $P_{F,k}$, processing of forming the final arc $L_{F,k}$ is simplified.

It is to be noted that each final arc $L_{F,j}$ other than the final arc $L_{F,k}$ is also formed using the interpolation function $L_{F,j}(t)$. The interpolation function $L_{F,j}(t)$ is calculated using expressions obtained by substituting j for k in Expression (37) to Expression (42). In this case, the curve interpolation is carried out between final positions $P_{F,i}$ of the respective sensor units $S_i$ at a constant angular velocity with respect to a change in the parametric variable of the interpolation function $L_{F,j}(t)$. When all the final arcs $L_{F,j}$ are formed, the final curve form 85 of the inserting section 11 of the endoscope 10 is detected.

As shown in FIG. 4, when the final curve form 85 is detected by the final curve form detecting section 65, whether the inspection by the endoscopic form detection device 1 is completed is confirmed (a step S108). When the inspection is not completed (the step S108—No), the processing returns to the step S101 to perform the next form detection of the inserting section 11 of the endoscope 10 in the stationary state. When the inspection is completed (the step S108—Yes), the form detection of the inserting section 11 of the endoscope 10 is terminated.

Therefore, the endoscopic form detection device 1 having the above-described configuration and the form detecting method of the inserting section 11 of the endoscope 10 using the endoscopic form detection device 1 exhibit the following effects. That is, in the endoscopic form detection device 1, the posture detecting section 30 is configured to detect a posture of each sensor unit $S_i$ from measurement data of the respective sensor units $S_i$, and the sensor tentative position detecting section 40 is configured to detect a tentative position $P_{0,i}$ of each sensor unit $S_i$ from the posture of each sensor unit $S_i$. Furthermore, the tentative curve form detecting section 50 is configured to perform the curve interpolation between the tentative positions $P_{0,i}$ of the respective sensor units $S_i$ using the tentative arc $L_{0,j}$, thereby detecting the tentative curve form 75. Moreover, the sensor position correcting section 55 is configured to correct a position of each sensor unit $S_i$ based on an absolute value of a difference between the arc length $R_{0,j}\phi_{0,j}$ of each tentative arc $L_{0,j}$ of the tentative curve form 75 and the inter-sensor dimension l. Additionally, the final curve form detecting section 65 is configured to perform the curve interpolation between final positions $P_{F,i}$ of the respective sensor units $S_i$, that have been subjected to the positional correction, by using the final arc $L_{F,j}$, thereby detecting the final curve form 85. As described above, since the final curve form 85 of the inserting section 11 is detected from the measurement data of the sensor units $S_i$ arranged in the inserting section 11 configured to be inserted into a body cavity at the time of observation, a sense coil and other parts do not have to be provided outside a body. Therefore, miniaturization and simplification of the endoscopic form detection device 1 can be realized.

Additionally, when correcting a position of each sensor unit $S_i$ by the sensor position sequentially compensating section 57, the sensor moving section 61 is configured to move the sensor unit $S_i$ from the pre-movement position $Q_{t-1,i}$ to the post-movement position $Q_{t,i}$. Further, the post-movement arc forming section 62 is configured to perform the curve interpolation between the final position $P_{F,i-1}$ of the sensor unit $S_{i-1}$ provided to be adjacent to the proximal end side of the sensor unit $S_i$ and the post-movement position $Q_{t,i}$ of the sensor unit $S_i$ to form the post-movement arc $L_{t,j}$ every time the sensor moving section 61 moves the sensor unit $S_i$ once. Furthermore, after the post-movement arc $L_{t,j}$ is formed, the movement controlling section 63 is configured to calculate the energy $E_{t,j}$, which is an absolute value of a difference between the arc length $R_{t,j}\phi_{t,j}$ of the post-movement arc $L_{t,j}$ and the inter-sensor dimension l. When the energy $E_{t,j}$ is higher than the predetermined threshold value, the sensor moving section 61 further moves the sensor unit $S_i$ from the position $Q_{t,i}$. When the energy $E_{t,j}$ is not higher than the predetermined threshold value, the final position deciding section 64 is configured to decide the post-movement position $Q_{F,i}$ in the last movement of the sensor unit $S_i$ effected by the sensor moving section 61 as the final position $P_{F,i}$ of the sensor unit $S_i$, which is the compensation target sensor 81. That is, the sensor moving section 61 is configured to repeatedly move the sensor unit $S_i$ until the energy $E_{t,j}$ becomes equal to or below the predetermined threshold value. As described above, since the sensor position sequentially compensating section 57 is configured to perform the positional compensation of the respective sensor units $S_i$ based on the inter-sensor dimension l which is an actual dimension between the respective sensor units $S_i$, the final curve form 85 having less errors as compared with an actual form of the inserting section 11 can be detected. As a result, the final curve form 85 of the inserting section 11 can be highly accurately detected.

Moreover, when the sensor position correcting section 55 corrects the position of the sensor unit $S_i$, the form between the sensor unit $S_{i-1}$ provided to be adjacent to the proximal end side of the sensor unit $S_i$ and the sensor unit $S_i$ alone is affected, whereby the tentative arc $L_{0,j}$ is corrected to the final arc $L_{F,j}$. That is, the entire form of the inserting section 11 is not corrected every time the positional correction of one sensor unit $S_i$ is performed. Here, the inter-sensor dimension l is a dimension between the respective sensor units $S_i$ in the longitudinal directions, and it is a local parameter of the inserting section 11. That is, the inter-sensor dimension l is not a parameter that affects the entire form of the inserting section 11 but a parameter that locally affects the form of the inserting section 11. Therefore, since the form of the inserting section 11 is locally corrected near one sensor unit $S_i$ that has been subjected to the positional correction by the positional correction of the one sensor unit $S_i$, the tentative arc $L_{0,j}$ is highly accurately corrected to the final arc $L_{F,j}$. As a result, the final curve form 85 of the inserting section 11 can be highly accurately detected. Moreover, since the form of the inserting section 11 can be locally corrected near the position-corrected sensor unit $S_i$ alone by the positional correction of the one sensor unit $S_i$, the processing of correcting the form of the inserting section 11 can be simplified.

Additionally, in the final curve form detecting section 65, the curve interpolation is effected between the final positions $P_{F,i}$ of the respective sensor units $S_i$ by changing t from 0 to 1 with use of the interpolation function $L_{F,j}(t)$, whereby each final arc $L_{F,j}$ is formed. At this time, the curve interpolation is carried out between the final positions $P_{F,i}$ of the respective sensor units $S_i$ at a constant angular velocity with respect to a change in the parametric variable t. Therefore, when performing the interpolation between the respective final positions $P_{F,i}$, since a change in angular velocity does not have to be taken into consideration, the processing of forming each final arc $L_{F,j}$ can be simplified.

Further, in the endoscopic form detection device 1, an acceleration sensor $A_i$ is configured to measure gravitational acceleration and a geomagnetic sensor $B_i$ is configured to measure geomagnetism in the stationary state in which the inserting section 11 is not moving. Furthermore, the posture detecting section 30 is configured to detect a posture of each sensor unit $S_i$ from the measured gravitational acceleration and geomagnetism. In the stationary state, each of the gravitational acceleration and the geomagnetism has a fixed intensity in a fixed direction. Since a posture of each sensor unit $S_i$ is detected from the gravitational acceleration and the geomagnetism, the posture of the sensor unit $S_i$ can be highly accurately detected even in the stationary state. As a result, the final curve form 85 of the inserting section 11 can be highly accurately detected.

Second Embodiment

A second embodiment according to the present invention will now be described with reference to FIG. 19. It is to be noted that like reference numerals denote the same parts or parts having the same functions as those in the first embodiment, thereby omitting description thereof.

Like the first embodiment, a sensor position correcting section 55 according to this embodiment includes a sensor position sequentially compensating section 57 configured to sequentially perform positional compensation from a pre-compensation position $Q_{0,i}$ to a final position $P_{F,i}$ of each sensor unit $S_i$ starting from a sensor unit $S_i$ provided on a proximal end side (a side close to an origin of a global coordinate system C), and an uncompensated sensor group moving section 59 configured to parallel translate an uncompensated sensor group 77, that includes the sensor units $S_i$ which have not been subjected to the positional compensation, every time the sensor position sequentially compensating section 57 performs the positional compensation of one sensor unit $S_i$.

Like the first embodiment, the sensor position sequentially compensating section 57 includes a sensor moving section 61 configured to move a compensation target sensor 81, which is a positional compensation target, from the pre-compensation position $Q_{0,i}$ more than once. Based on the movement performed by the sensor moving section 61 once, the compensation target sensor 81 moves from a pre-movement position $Q_{t-1,i}$ to a post-movement position $Q_{t,i}$. Furthermore, the sensor position sequentially compensating section 57 includes a post-movement arc forming section 62 configured to perform curve interpolation between a final position $P_{F,i-1}$ of a close-side adjacent sensor 82, that is a sensor unit $S_i$ provided to be adjacent to the proximal end side (the side close to the origin of the global coordinate system C) with respect to the compensation target sensor 81, and a post-movement position $Q_{t,i}$ of the compensation target sensor 81 every time the sensor moving section 61 moves the compensation target sensor 81 once. When the curve interpolation is performed between the final position $P_{F,i-1}$ of the close-side adjacent sensor 82 and the post-movement position $Q_{t,i}$ of the compensation target sensor 81 by the post-movement arc forming section 62, a post-movement arc $L_{t,j}$ is formed.

The sensor position sequentially compensating section 57 includes a movement controlling section 63 configured to control the sensor moving section 61 to repeat the movement of the compensation target sensor 81 for a predetermined number of times so that an absolute value of a difference between an arc length $R_{t,j}\phi_{t,j}$ of a post-movement arc $L_{t,j}$ and an inter-sensor dimension l becomes smaller than an absolute value of a difference between an arc length $R_{t-1,j}\phi_{t-1,j}$ of a pre-movement arc $L_{t-1,j}$, which is formed by performing the curve interpolation between the final position $P_{F,i-1}$ of the close-side adjacent sensor 82 and the pre-movement position $Q_{t-1,i}$ of the compensation target sensor 81, and the inter-sensor dimension l. Here, the absolute value of the difference between the arc length $R_{t-1,j}\phi_{t-1,j}$ of the pre-movement arc $L_{t-1,j}$ and the inter-sensor dimension l is determined to be energy $E_{t-1,j}$. Likewise, the absolute value of the difference between the arc length $R_{t,j}\phi_{t,j}$ of the post-movement arc $L_{t,j}$ and the inter-sensor dimension l is determined to be energy $E_{t,j}$. Furthermore, the sensor position sequentially compensating section 57 includes a final position deciding section 64 configured to decide a post-movement position $Q_{F,i}$ in last movement effected by the sensor moving section 61 as a final position $P_{F,i}$ of the compensation target sensor 81.

Description will now be given as to a method of correcting a position of each sensor unit $S_i$ by the sensor position correcting section 55. Like the first embodiment, the sensor position correcting section 55 is configured to correct a position of each sensor unit $S_i$ based on an absolute value of a difference between an arc length $R_{0,j}\phi_{0,j}$ of each tentative arc $L_{0,j}$ of the tentative curve form 75 detected by a tentative curve form detecting section 50 and the inter-sensor dimension l (the step S106 in FIG. 4). That is, the position of each sensor unit $S_i$ is corrected based on energy $E_{0,j}$ obtained by Expression (22). As a result, each sensor unit $S_i$ is corrected from the tentative position $P_{0,i}$ to the final position $P_{F,i}$.

Figure 19:
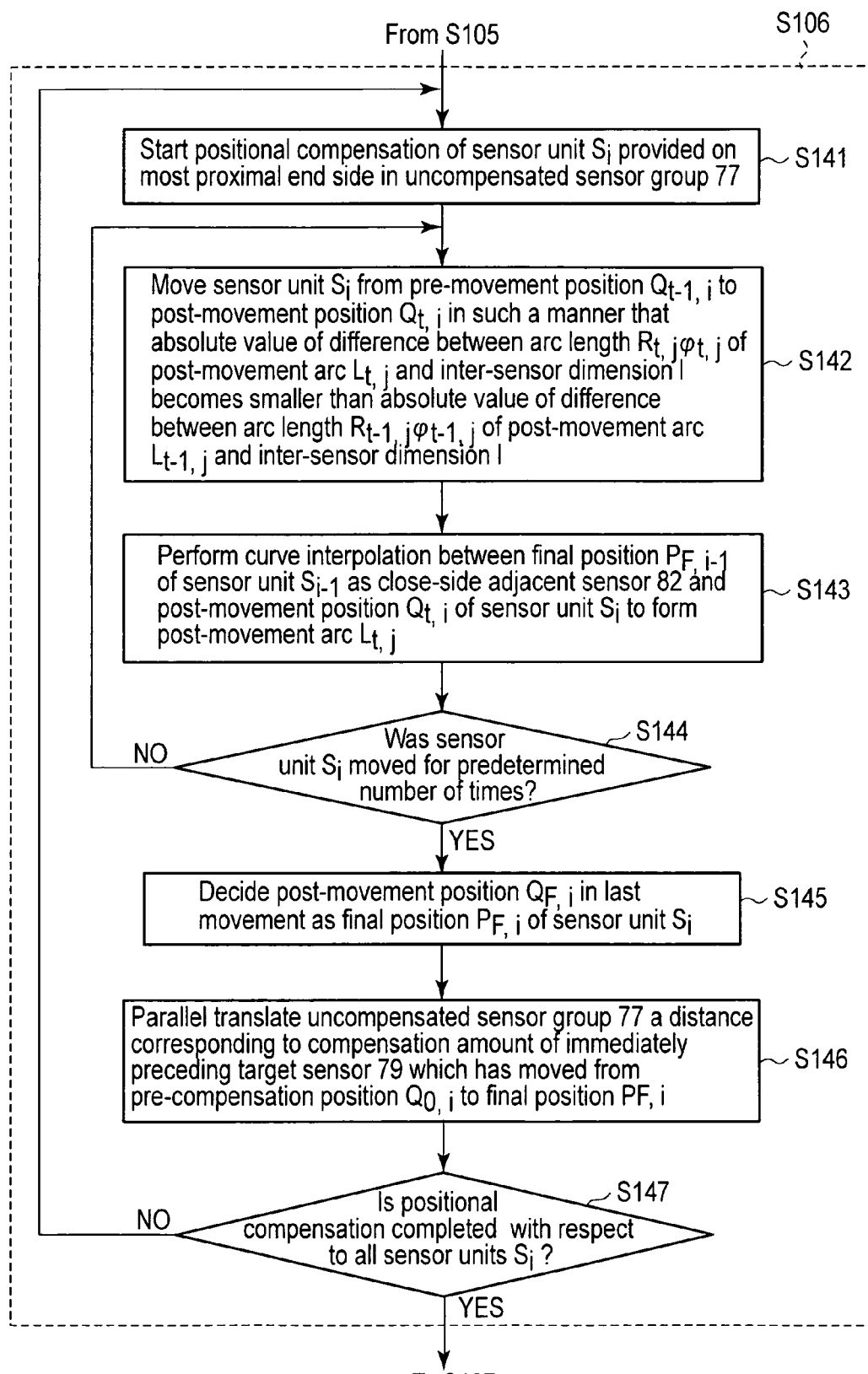
FIG. 19 is a flowchart showing a method of correcting positions of respective sensor units by a sensor position correcting section of an endoscopic form detection device according to a second embodiment of the present invention.

FIG. 19 is a flowchart showing a method of correcting a position of each sensor unit $S_i$ by the sensor position correcting section 55. As shown in FIG. 19, when correcting a position of each sensor unit $S_i$, like the first embodiment, the sensor position sequentially compensating section 57 is configured to sequentially carry out the positional compensation from the pre-compensation position $Q_{0,\,i}$ to the final position $P_{F,\,i}$ of each of the sensor units $S_i$ starting from the sensor unit $S_i$ provided on the proximal end side (the side close to the origin of the global coordinate system C). The sensor position sequentially compensating section 57 starts the positional compensation of the sensor unit $S_i$ provided on the most proximal end side in an uncompensated sensor group 77 (a step S141). That is, if the positional compensation from the pre-compensation position $Q_{0,\,i}$ to the final position $P_{F,\,i}$ is completed from the first sensor unit to the sensor unit $S_{k-1}$, the sensor position sequentially compensating section 57 is configured to start the positional compensation to the final position $P_{F,\,k}$ of the sensor unit $S_k$ provided on the most proximal end side in the uncompensated sensor group 77. In this case, the sensor unit $S_k$ is a compensation target sensor 81 as a positional compensation target. It is to be noted that the positional compensation of a (k+1)th sensor unit $S_k$ from the proximal end side will now be described hereinafter.

When starting the positional compensation of the sensor unit $S_k$ as the compensation target sensor 81, the positional compensation to the final position $P_{F,\,i}$ is completed from the first sensor unit to the sensor unit $S_{k-1}$. At this time, the sensor unit $S_k$ is placed at a pre-compensation position $Q_{0,\,k}$. In this state, the sensor moving section 61 is configured to move the sensor unit $S_k$ from the position $Q_{0,\,k}$ to a position $Q_{1,\,k}$ (a step S142), whereby the sensor unit $S_k$ is moved for the first time. The sensor moving section 61 is configured to move the sensor unit $S_k$ more than once. Moreover, in the sth movement, the sensor unit $S_k$ as the compensation target sensor 81 moves from a pre-movement position $Q_{s-1,\,k}$ to a post-movement position $Q_{s,\,k}$. That is, the sensor unit $S_k$ moves from a pre-movement position $Q_{t-1,\,k}$ to a post-movement position $Q_{t,\,k}$ by the movement performed once by the sensor moving section 61 (the step S142).

Additionally, the post-movement arc forming section 62 is configured to carry out the curve interpolation between a final position $P_{F,\,k-1}$ of the sensor unit $S_{k-1}$, provided to be adjacent to the proximal end side of the sensor unit $S_k$, and the post-movement position $Q_{t,\,k}$ of the sensor unit $S_k$ every time the sensor moving section 61 moves the sensor unit $S_k$ once, thereby forming a post-movement arc $L_{t,\,k}$ (a step S143). After the sth movement, the curve interpolation is carried out between the final position $P_{F,\,k-1}$ of the sensor unit $S_{k-1}$ and the post-movement position $Q_{s,\,k}$ of the sensor unit $S_k$, thereby forming a post-movement arc $L_{s,\,k}$. Here, the sensor unit $S_{k-1}$ is the close-side adjacent sensor 82 provided to be adjacent to the side close to the origin of the global coordinate system C with respect to the sensor unit $S_k$, which is the compensation target sensor 81.

When forming the post-movement arc $L_{s,\,k}$ after the sth movement of the sensor unit $S_k$, like the first embodiment, Expression (23.1) to Expression (28) are used to calculate a parameter of the post-movement arc $L_{s,\,k}$. Further, the calculated parameter is used to form the post-movement arc $L_{s,\,k}$ between the final position $P_{F,\,k-1}$ and the post-movement position $Q_{s,\,k}$.

It is to be noted that the processing of forming the post-movement arc $L_{s,\,k}$ after the sth movement of the sensor units $S_k$ has been described, and the post-movement arc $L_{t,\,k}$ between the final position $P_{F,\,k-1}$ of the sensor unit $S_{k-1}$ and the post-movement position $Q_{t,\,k}$ of the sensor unit $S_k$ is likewise formed after movement other than the sth movement of the sensor unit $S_k$ by using dimensions obtained by substituting t for s in Expression (23.1) to Expression (28).

The sensor moving section 61 is controlled by a movement controlling section 63 to move the compensation target sensor 81 so that an absolute value of a difference between an arc length $R_{t,\,k}\phi_{t,\,k}$ of a post-movement arc $L_{t,\,k}$ and the inter-sensor dimension l becomes smaller than an absolute value of a difference between an arc length $R_{t-1,\,k}\phi_{t-1,\,k}$ of a pre-movement arc $L_{t-1,\,k}$, which is formed by performing the curve interpolation between the final position $P_{F,\,k-1}$ of the close-side adjacent sensor 82 and the pre-movement position $Q_{t-1,\,k}$ of the compensation target sensor 81, and the inter-sensor dimension l. Here, the absolute value of the difference between the arc length $R_{t,\,k}\phi_{t,\,k}$ of the post-movement arc $L_{t,\,k}$ and the inter-sensor dimension l is determined to be energy $E_{t,\,k}$, and this energy is given by Expression (29) like the first embodiment. Further, the absolute value of the difference between the arc length $R_{t-1,\,k}\phi_{t-1,\,k}$ of the pre-movement arc $L_{t-1,\,k}$ and the inter-sensor dimension l is determined to be energy $E_{t-1,\,k}$, and this energy is given by an expression obtained by substituting t−1 for t in Expression (29). That is, the sensor moving section 61 is configured to move the sensor unit $S_k$ as the compensation target sensor 81 in such a manner that the energy $E_{t,\,k}$ after the movement becomes smaller than the energy $E_{t-1,\,k}$ before the movement (a step S142). It is to be noted that, for example, a pre-movement arc $L_{s-1,\,k}$ in the sth movement of the sensor unit $S_k$ is equal to a post-movement arc $L_{s-1,\,k}$ in the (s−1)th movement of the sensor unit $S_k$. The pre-movement arc $L_{s-1,\,k}$ in the sth movement of the sensor unit $S_k$ is formed using expressions obtained by substituting s−1 for s in Expression (23.1) to Expression (28).

Furthermore, the movement controlling section 63 is configured to judge whether the sensor unit $S_k$ as the compensation target sensor 81 has been moved for a predetermined number of times (a step S144). If the sensor unit $S_k$ has not been moved for the predetermined number of times (the step S144—No), the processing returns to the step S122, and the sensor moving section 61 further moves the sensor unit $S_k$ from the position $Q_{t,\,k}$. In this case, after the sth movement of the sensor unit $S_k$, the sensor moving section 61 is configured to carry out (s+1) the movement. Based on the (s+1)th movement, the sensor unit $S_k$ is moved from a pre-movement position $Q_{s,\,k}$ to a post-movement position $Q_{s+1,\,k}$. As described above, the sensor moving section 61 is controlled by the movement controlling section 63 to repeatedly perform the movement of the sensor unit $S_k$ as the compensation target sensor 81 from the pre-movement position $Q_{t-1,\,k}$ to the post-movement position $Q_{t,\,k}$ for the predetermined number of times.

If the sensor unit $S_k$ has been moved for the predetermined number of times (the step S144—Yes), the processing advances to the next step. Furthermore, a final position deciding section 64 is configured to decide the post-movement position $Q_{F,\,k}$ in last (e.g., Fth) movement of the sensor unit $S_k$ by the sensor moving section 61 as a final position $P_{F,\,k}$ of the sensor unit $S_k$ (a step S145), which is the compensation target sensor 81. As described above, the positional correction of the sensor unit $S_k$ to the final position $P_{F,\,k}$ is completed.

It is to be noted that the sensor position sequentially compensating section 57 performs the positional compensation to a final position $P_{i,\,k}$ with respect to each sensor unit $S_i$ other than the sensor unit $S_k$ like the sensor unit $S_k$. That is, the sensor moving section 61 is configured to move the sensor unit $S_i$ from a pre-movement position $Q_{t-1,\,i}$ to a post-movement position $Q_{t,\,i}$ (the step S142). Further, the post-movement arc forming section 62 is configured to perform the curve interpolation between a final position $P_{F,\,i-1}$ of a sensor unit $S_{i-1}$ provided to be adjacent to the proximal end side of the sensor unit $S_i$ and the post-movement position $Q_{t,\,i}$ of the sensor unit $S_i$ every time the sensor moving section 61 moves the sensor unit $S_i$ once, thereby forming a post-movement arc $L_{t,\,j}$ (the step S143). The sensor moving section 61 is configured to move the sensor unit $S_i$ in such a manner that an absolute value of a difference between an arc length $R_{t,j}\phi_{t,j}$ of the post-movement arc $L_{t,j}$ and the inter-sensor dimension l becomes smaller than an absolute value of a difference between an arc length $R_{t-1,j}\phi_{t-1,j}$ of a pre-movement arc $L_{t-1,j}$ and the inter-sensor dimension l (a step S142). That is, the sensor unit $S_i$ as the compensation target sensor 81 is moved in such a manner that the energy $E_{t,j}$ after the movement becomes smaller than the energy $E_{t-1,j}$ before the movement.

Moreover, after forming the post-movement arc $L_{t,j}$, the movement controlling section 63 is configured to judge whether the sensor unit $S_i$ has been moved for a predetermined number of times (the step S144). If the sensor unit $S_i$ has not been moved for the predetermined number of times (the step S144—No), the processing returns to the step S142, and the sensor moving section 61 further moves the sensor unit $S_i$ from the position $Q_{t,i}$. If the sensor unit $S_i$ has been moved for the predetermined number of times (the step S144—Yes), the processing advances to the next step. Furthermore, the final position deciding section 64 is configured to decide the post-movement position $Q_{F,i}$ in last movement of the sensor unit $S_i$ effected by the sensor moving section 61 as a final position $P_{F,i}$ of the sensor unit $S_i$ (the step S145), which is the compensation target sensor 81. As described above, the positional compensation of the sensor unit $S_i$ to the final position $P_{F,i}$ is completed.

Moreover, like the first embodiment, the uncompensated sensor group moving section 59 is configured to parallel translate an uncompensated sensor group 77, that includes the sensor units $S_i$ which have not been subjected to the positional compensation, every time the sensor position sequentially compensating section 57 performs the positional compensation of one sensor unit Si (a step S146). Since the processing in the uncompensated sensor group moving section 59 is the same as that in the first embodiment, detailed description will be omitted.

Additionally, whether the positional compensation is completed with respect to all the sensor units $S_i$ is confirmed (a step S147). If the positional compensation is completed with respect to all the sensor units $S_i$ (the step S147—Yes), the processing advances to the next step. If the positional compensation is not completed with respect to all the sensor units $S_i$ (the step S147—No), the processing returns to the step S141, and the sensor position sequentially compensating section 57 performs the positional compensation of the sensor unit $S_i$ provided on the most proximal end side in the uncompensated sensor group 77. That is, the steps S141 to S146 are repeatedly carried out until the positional compensation is completed with respect to all the sensor units $S_i$.

Therefore, the endoscopic form detection device 1 having the above-described configuration and the form detecting method of the inserting section 11 of the endoscope 10 using the endoscopic form detection device 1 exhibit the following effects in addition to the same effects as those in the first embodiment. That is, in the endoscopic form detection device 1, when compensating a position of each sensor unit $S_i$ by the sensor position sequentially compensating section 57, the sensor moving section 61 is configured to move the sensor unit $S_i$ from the pre-movement position $Q_{t-1,i}$ to the post-movement position $Q_{t,i}$. Further, the post-movement arc forming section 62 is configured to carry out the curve interpolation between the final position $P_{F,i-1}$ of the sensor unit $S_{i-1}$, provided to be adjacent to the proximal end side of the sensor unit $S_i$, and the post-movement position $Q_{t,i}$ of the sensor unit $S_i$ every time the sensor moving section 61 moves the sensor unit $S_i$ once, thereby forming the post-movement arc $L_{t,j}$. The sensor moving section 61 is configured to move the sensor unit $S_i$ as the compensation target sensor 81 in such a manner that the absolute value of the difference between the arc length $R_{t,j}\phi_{t,j}$ of the post-movement arc $L_{t,j}$ and the inter-sensor dimension l becomes smaller than the absolute value of the difference between the arc length $R_{t-1,j}\phi_{t-1,j}$ of the pre-movement arc $L_{t-1,j}$ and the inter-sensor dimension l. Furthermore, after the post-movement arc $L_{t,j}$ is formed, the movement controlling section 63 is configured to judge whether the sensor unit $S_i$ has been moved for the predetermined number of times. If the sensor unit $S_i$ has not been moved for the predetermined number of times, the sensor moving section 61 further moves the sensor unit $S_i$ from the position $Q_{t,i}$. If the sensor unit $S_i$ has been moved for the predetermined number of times, the final position deciding section 64 is configured to decide the post-movement position $Q_{F,i}$ in the last movement of the sensor unit $S_i$ performed by the sensor moving section 61 as the final position $P_{F,i}$ of the sensor unit $S_i$, which is the compensation target sensor 81. That is, the sensor moving section 61 is configured to repeatedly move the sensor unit $S_i$ until the sensor unit $S_i$ is moved for the predetermined number of times. As described above, since the sensor position sequentially compensating section 57 carries out the positional compensation of each sensor unit $S_i$ based on the inter-sensor dimension l which is the actual dimension between the respective sensor units $S_i$, the final curve form 85 having less error as compared with an actual form of the inserting section 11 can be detected. As a result, the final curve form 85 of the inserting section 11 can be highly accurately detected.

(Modification)

It is to be noted that each local coordinate system $C_i$ is a coordinate system in which $Y_i$ axis directions coincide with the longitudinal directions at the center of a sensor unit $S_i$ in the foregoing embodiments. However, each local coordinate system $C_i$ can be a coordinate system in which an origin is set at the center of the sensor unit $S_i$ and any one of an $X_i$ axis, a $Y_i$ axis, and a $Z_i$ axis is a longitudinal axis whose axial directions coincide with the longitudinal directions at the center of the sensor unit $S_i$. However, when the $X_i$ axis is the longitudinal axis, the following representations are used in place of Expression (16.1) and Expression (16.2):

$$i_k = [\,1_{xk}\ \ 1_{yk}\ \ 1_{zk}\,]^T \quad (43.1)$$
$$= 1 C^G_{Bk-1} \hat{f}_{xk-1}$$
$$= 1 \begin{bmatrix} -\sin\gamma_{k-1}\cdot\sin\alpha_{k-1}\cdot\sin\beta_{k-1}+\cos\beta_{k-1}\cdot\cos\gamma_{k-1} \\ \cos\gamma_{k-1}\cdot\sin\alpha_{k-1}\cdot\sin\beta_{k-1}+\cos\beta_{k-1}\cdot\sin\gamma_{k-1} \\ -\cos\alpha_{k-1}\cdot\sin\beta_{k-1} \end{bmatrix}$$

$$\hat{f}_{xh-1} = [\,1\ \ 0\ \ 0\,]^T \quad (43.2)$$

Likewise, when the $Z_i$ axis is the longitudinal axis, the following expressions are used in place of Expression (16.1) and Expression (16.2):

$$i_k = [\,1_{xk}\ \ 1_{yk}\ \ 1_{zk}\,]^T \quad (44.1)$$
$$= 1 C^G_{Bk-1} \hat{f}_{zk-1}$$
$$= 1 \begin{bmatrix} \sin\gamma_{k-1}\cdot\cos\alpha_{k-1}\cdot\cos\beta_{k-1}+\sin\beta_{k-1}\cdot\cos\gamma_{k-1} \\ -\cos\gamma_{k-1}\cdot\sin\alpha_{k-1}\cdot\cos\beta_{k-1}+\cos\beta_{k-1}\cdot\sin\gamma_{k-1} \\ \cos\alpha_{k-1}\cdot\cos\beta_{k-1} \end{bmatrix}$$

$$\hat{f}_{zk-1} = [\,0\ \ 0\ \ 1\,]^T \quad (44.2)$$

Here, a vector in Expression (43.2) is a unit vector in $X_{k-1}$ axis directions which are the longitudinal directions at an origin of a local coordinate system $C_{k-1}$, and a vector in Expression (44.2) is a unit vector in $Z_{k-1}$ axis directions which are the longitudinal direction at the origin of the local coordinate system $C_{k-1}$.

Further, in the foregoing embodiments, the global coordinate system C is a coordinate system in which an origin is set at the center of a sensor unit $S_0$ on the most proximal end side, Z axis directions coincide with the vertical directions, and an X axis and a Y axis are arranged on the horizontal plane. However, it is possible to adopt a coordinate system in which any one of an X axis, a Y axis, and a Z axis is a vertical axis whose axial directions coincide with the vertical directions and two axes other than the vertical axis are horizontal axes which are arranged on the horizontal plane. As a result, the posture detecting section 30 can detect a posture of each sensor unit $S_i$ based on gravitational acceleration measured by an acceleration sensor $A_i$ and geomagnetism measured by a geomagnetic sensor $B_i$. However, when the X axis is the vertical axis, an X axis component, a Y axis component, and a Z axis component in the global coordinate system C of a gravitational acceleration vector represented by Expression (2) are as follows:

$$\dot{a}_{th} = [-g\ 0\ 0]^T \quad (45)$$

In this case, although the posture angles $\alpha_i$, $\beta_i$, and $\gamma_i$ are of the (Z, X, Y) type that rotate in the order of the yaw angle $\gamma_i$, the pitch angle $\alpha_i$, and the roll angle $\beta_i$ in the first embodiment, the rotation order of the posture angles $\alpha_i$, $\beta_i$, and $\gamma_i$ is changed, and a rotation matrix different from the rotation matrix in Expression (1) is used. As a result, the posture angles $\beta_i$ and $\gamma_i$ about the Y axis and the Z axis which are horizontal axes can be calculated by the first angle calculating section 34 based on acceleration data measured by the acceleration sensor $A_i$. Furthermore, the posture angle $\alpha_i$ about the X axis which is a vertical axis can be calculated by the second angle calculating section 36 based on geomagnetic data measured by the geomagnetic sensor $B_i$. This operation is likewise performed when the Y axis is the vertical axis, and the posture angles $\alpha_i$ and $\gamma_i$ about the X axis and the Z axis which are the horizontal axes are calculated by the first angle calculating section 34 based on the acceleration data measured by the acceleration sensor $A_i$. Furthermore, the posture angle $\beta_i$ about the Y axis which is the vertical axis is calculated by the second angle calculating section 36 based on the geomagnetic data measured by the geomagnetic sensor $B_i$.

Moreover, although the origin of the global coordinate system C is set at the center of the sensor unit $S_0$ on the most proximal end side in the foregoing embodiments, the origin may be set at the center of the sensor unit $S_N$ on the most distal end side. In this case, a link forming section 41 uses expressions obtained by substituting j+1 for k in Expression (16.1) and Expression (16.2) to obtain a vector extending toward a sensor unit $S_{j-1}$ on a proximal end side (a side far from the origin of the global coordinate system C) of a tentative link $T_{0,j}$ from a sensor unit $S_j$ on a distal end side (a side close to the origin of the global coordinate system C) of the tentative link $T_{0,j}$. Additionally, the tentative link $T_{0,j}$ is formed by the vector extending from the sensor unit $S_j$ to the sensor unit $S_{j-1}$. That is, the tentative link forming section 41 is configured to form the tentative link $T_{0,j}$ on the assumption that the tentative link $T_{0,j}$ is extended in the longitudinal directions at the center of the sensor unit $S_j$ from the center of the sensor unit $S_j$ on the distal end side (the side close to the origin of the global coordinate system C) to the center of the sensor unit $S_{j-1}$ on the proximal end side (the side far from the origin of the global coordinate system C). Further, when performing the positional compensation of each sensor unit $S_i$ by the sensor position sequentially compensating section 57 of the sensor position correcting section 55, the positional compensation is sequentially carried out from the sensor unit $S_i$ on the distal end side (the side close to the origin of the global coordinate system C). In this case, the sensor unit $S_i$ provided to be adjacent to the distal end side (the side close to the origin of the global coordinate system C) of the compensation target sensor 81 is a close-side adjacent sensor 82.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic form detection device comprising:
   an endoscope including an inserting section in which sensor units are arranged in longitudinal directions at intervals of a predetermined inter-sensor dimension;
   a posture detecting section configured to detect a posture of each of the sensor units based on measurement data in the sensor unit;
   a sensor tentative position detecting section configured to detect a tentative position of each sensor unit on the assumption that a portion between the respective sensor units is a linear tentative link whose dimension is equal to the inter-sensor dimension based on the posture of each sensor unit detected by the posture detecting section;
   a tentative curve form detecting section configured to perform curve interpolation between the tentative positions of the respective sensor units by using a tentative arc to detect a tentative curve form of the inserting section based on the tentative positions of the respective sensor units detected by the sensor tentative position detecting section;
   a sensor position correcting section configured to correct a position of each sensor unit from the tentative position to a final position based on an absolute value of a difference between an arc length of each tentative arc of the tentative curve form detected by the tentative curve form detecting section and the inter-sensor dimension; and
   a final curve form detecting section configured to perform curve interpolation between the final positions of the respective sensor units by using a final arc to detect a final curve form of the inserting section.

2. The device according to claim 1,
   wherein the tentative curve form detecting section includes:
   a unit tangent vector calculating section configured to calculate a unit tangent vector at the tentative position of each sensor unit;
   a rate-of-change calculating section configured to calculate a rate of change of the unit tangent vector between the tentative positions of the respective sensor units based on each unit tangent vector calculated by the unit tangent vector calculating section; and
   a tentative arc forming section configured to form the tentative arc between the tentative positions of the respective sensor units based on each unit tangent vector calculated by the unit tangent vector calculating section and each rate of change calculated by the rate-of-change calculating section.

3. The device according to claim 1,
wherein the sensor position correcting section includes:
a sensor position sequentially compensating section configured to sequentially perform positional compensation starting from the sensor unit provided on a side close to an origin of a global coordinate system, that has the origin set at the center of the sensor unit on the most proximal end side or the most distal end side, to compensate a position of each sensor unit from a pre-compensation position before the positional compensation to the final position in the global coordinate system; and
an uncompensated sensor group moving section configured to parallel translate an uncompensated sensor group, that includes the sensor units which have not been subjected to the positional compensation, a distance corresponding to a compensation amount from the pre-compensation position to the final position of an immediately preceding compensation target sensor, that is the sensor unit that is a compensation target in immediately preceding positional compensation, every time the sensor position sequentially compensating section performs the positional compensation of one sensor unit.

4. The device according to claim 3,
wherein the sensor position sequentially compensating section includes:
a sensor moving section configured to move a compensation target sensor, that is a positional compensation target, from the pre-compensation position more than once to thereby move the compensation target sensor from a pre-movement position to a post-movement position by the movement performed once; and
a post-movement arc forming section configured to perform curve interpolation between the final position of a close-side adjacent sensor, that is the sensor unit provided to be adjacent to a side close to the origin of the global coordinate system with respect to the compensation target sensor, and the post-movement position of the compensation target sensor to form a post-movement arc every time the sensor moving section moves the compensation target sensor once.

5. The device according to claim 4,
wherein the sensor position sequentially compensating section includes:
a movement controlling section configured to control the sensor moving section to repeatedly move the compensation target sensor from the pre-movement position to the post-movement position until an absolute value of a difference between an arc length of the post-movement arc formed by the post-movement arc forming section and the inter-sensor dimension becomes equal to or below a predetermined threshold value; and
a final position deciding section configured to decide the post-movement position in last movement by the sensor moving section as the final position of the compensation target sensor.

6. The device according to claim 4,
wherein the sensor position sequentially compensating section includes:
a movement controlling section configured to control the sensor moving section to repeatedly move the compensation target sensor for a predetermined number of times so that an absolute value of a difference between an arc length of the post-movement arc and the inter-sensor dimension becomes smaller than an absolute value of a difference between an arc length of a pre-movement arc, which is formed by performing curve interpolation between the final position of the close-side adjacent sensor and the pre-movement position of the compensation target sensor, and the inter-sensor dimension; and
a final position deciding section configured to decide the post-movement position in last movement by the sensor moving section as the final position of the compensation target sensor.

7. The device according to claim 1,
wherein the final curve form detecting section includes:
a parameter calculating section configured to calculate a parameter of each final arc based on the final position of each sensor unit; and
a final arc forming section configured to perform curve interpolation between the final positions of the respective sensor units with use of an interpolation function employing a quaternion and a parametric variable, based on the parameter calculated by the parameter calculating section, at a constant angular velocity with respect to a change in the parametric variable, thereby forming the final arc.

8. A form detecting method of an inserting section of an endoscope, comprising:
performing measurement by using sensor units which are arranged in an inserting section of an endoscope in longitudinal directions at intervals of a predetermined inter-sensor dimension;
detecting a posture of each of the sensor units based on measurement data in the sensor unit by using a posture detecting section;
detecting a tentative position of each sensor unit by using a sensor tentative position detecting section, on the assumption that a portion between the respective sensor units is a linear tentative link whose dimension is equal to the inter-sensor dimension, based on the posture of each sensor unit detected by the posture detecting section;
performing curve interpolation between the tentative positions of the respective sensor units with use of a tentative arc and detecting a tentative curve form of the inserting section, by using a tentative curve form detecting section, based on the tentative positions of the respective sensor units detected by the sensor tentative position detecting section;
correcting a position of each sensor unit from the tentative position to a final position, by using a sensor position correcting section, based on an absolute value of a difference between an arc length of each tentative arc of the tentative curve form detected by the tentative curve form detecting section and the inter-sensor dimension; and
performing curve interpolation between the final positions of the respective sensor units with use of a final arc and detecting a final curve form of the inserting section by using a final curve form detecting section.

9. The method according to claim 8,
wherein the detecting the tentative curve form by the tentative curve form detecting section includes:
calculating a unit tangent vector at the tentative position of each sensor unit by using a unit tangent vector calculating section of the tentative curve form detecting section;
calculating a rate of change of the unit tangent vector between the tentative positions of the respective sensor units, by using a rate-of-change calculating section of the tentative curve form detecting section, based on each unit tangent vector calculated by the unit tangent vector calculating section; and
forming the tentative arc between the tentative positions of the respective sensor units, by using a tentative arc forming section of the tentative curve form detecting section, based on each unit tangent vector calculated by the unit tangent vector calculating section and each rate of change calculated by the rate-of-change calculating section.

10. The method according to claim 8,
wherein the correcting a position of each sensor unit from the tentative position to the final position by the sensor position correcting section includes:
sequentially performing positional compensation starting from the sensor unit provided on a side close to an origin of a global coordinate system, that has the origin set at the center of the sensor unit on the most proximal end side or the most distal end side, to compensate a position of each sensor unit from a pre-compensation position before the positional compensation to the final position, by using a sensor position sequentially compensating section of the sensor position correcting section, in the global coordinate system; and
parallel translating an uncompensated sensor group, that includes the sensor units which have not been subjected to the positional compensation, a distance corresponding to a compensation amount from the pre-compensation position to the final position of an immediately preceding compensation target sensor, that is the sensor unit that is a compensation target in immediately preceding positional compensation, by using an uncompensated sensor group moving section of the sensor position correcting section every time the sensor position sequentially compensating section performs the positional compensation of one sensor unit.

11. The method according to claim 10,
wherein the sequentially performing positional compensation of the respective sensor units from the sensor unit provided on the side close to the origin of the global coordinate system by the sensor position sequentially compensating section includes:
moving a compensation target sensor, that is a positional compensation target, from the pre-compensation position more than once to thereby move the compensation target sensor from a pre-movement position to a post-movement position, by using a sensor moving section of the sensor position sequentially compensating section, based on the movement performed once; and
performing curve interpolation between the final position of a close-side adjacent sensor, that is the sensor unit provided to be adjacent to a side close to the origin of the global coordinate system with respect to the compensation target sensor, and the post-movement position of the compensation target sensor to form a post-movement arc, by using a post-movement arc forming section of the sensor position sequentially compensating section, every time the sensor moving section moves the compensation target sensor once.

12. The method according to claim 11,
wherein the sequentially performing positional compensation of the respective sensor units from the sensor unit provided on the side close to the origin of the global coordinate system by the sensor position sequentially compensating section includes:
controlling the sensor moving section to repeatedly move the compensation target sensor from the pre-movement position to the post-movement position, by using a movement controlling section of the sensor position sequentially compensating section, until an absolute value of a difference between an arc length of the post-movement arc formed by the post-movement arc forming section and the inter-sensor dimension becomes equal to or below a predetermined threshold value; and
deciding the post-movement position in last movement by the sensor moving section as the final position of the compensation target sensor by using a final position deciding section of the sensor position sequentially compensating section.

13. The method according to claim 11,
wherein the sequentially performing positional compensation of the respective sensor units from the sensor unit provided on the side close to the origin of the global coordinate system by the sensor position sequentially compensating section includes:
controlling the sensor moving section to repeatedly move the compensation target sensor for a predetermined number of times, by using a movement controlling section of the sensor position sequentially compensating section, so that an absolute value of a difference between an arc length of the post-movement arc and the inter-sensor dimension becomes smaller than an absolute value of a difference between an arc length of a pre-movement arc, which is formed by performing curve interpolation between the final position of the close-side adjacent sensor and the pre-movement position of the compensation target sensor, and the inter-sensor dimension; and
deciding the post-movement position in last movement by the sensor moving section as the final position of the compensation target sensor by using a final position deciding section of the sensor position sequentially compensating section.

14. The method according to claim 8,
wherein detecting the final curve form of the inserting section by the final curve form detecting section includes:
calculating a parameter of each final arc, by using a parameter calculating section of the final curve form detecting section, based on the final position of each sensor unit; and
performing curve interpolation between the final positions of the respective sensor units with use of an interpolation function employing a quaternion and an parametric variable, based on the parameter calculated by the parameter calculating section, at a constant angular velocity with respect to a change in the parametric variable, thereby forming the final arc by using a final arc forming section of the final curve forming section.

* * * * *